United States Patent
Wei

(10) Patent No.: US 11,872,044 B2
(45) Date of Patent: Jan. 16, 2024

(54) ELECTROCARDIOGRAPH SYSTEM, ELECTROCARDIOGRAPHIC MEASUREMENT ELECTRODE, AND ELECTROCARDIOGRAPHIC MEASUREMENT METHOD

(71) Applicant: EKG TECHNOLOGY LAB, INC., Chiba (JP)

(72) Inventor: Daming Wei, Chiba (JP)

(73) Assignee: EKG TECHNOLOGY LAB, INC., Chiba (JP)

( * ) Notice: Subject to any disclaimer, the term of this patent is extended or adjusted under 35 U.S.C. 154(b) by 671 days.

(21) Appl. No.: 16/971,676

(22) PCT Filed: Feb. 21, 2018

(86) PCT No.: PCT/JP2018/006257
§ 371 (c)(1),
(2) Date: Aug. 20, 2020

(87) PCT Pub. No.: WO2019/163028
PCT Pub. Date: Aug. 29, 2019

(65) Prior Publication Data
US 2020/0405171 A1    Dec. 31, 2020

(51) Int. Cl.
*A61B 5/259*    (2021.01)
*A61B 5/339*    (2021.01)
(Continued)

(52) U.S. Cl.
CPC ............. *A61B 5/259* (2021.01); *A61B 5/002* (2013.01); *A61B 5/0006* (2013.01); *A61B 5/30* (2021.01);
(Continued)

(58) Field of Classification Search
None
See application file for complete search history.

(56) References Cited

U.S. PATENT DOCUMENTS 5,168,874 A    12/1992  Segalowitz
5,307,818 A     5/1994  Segalowitz
(Continued)

FOREIGN PATENT DOCUMENTS

JP    H07508903 A    10/1995
JP    2002034943 A    2/2002
(Continued)

OTHER PUBLICATIONS

JPO, International Search Report issued in IA Application No. PCT/JP2018/006257, dated May 29, 2018.

*Primary Examiner* — Carl H Layno
*Assistant Examiner* — Manolis Pahakis
(74) *Attorney, Agent, or Firm* — LKGlobal | Lorenz & Kopf LLP

(57) ABSTRACT

Provided is a wireless 12-lead or multiple unipolar-lead electrocardiograph system without cable connection between a measurement electrode and device body. The present invention includes a measurement electrode that acquires an electrocardiographic signal of a subject, a Wilson terminal that is connected to the measurement electrode and forms an indifferent electrode, and an electrocardiograph body that generates an electrocardiogram. The measurement electrode has active measurement electrodes that wirelessly communicate with the electrocardiograph body, and passive measurement electrodes that are connected to the active measurement electrodes, and the Wilson terminal. The electrocardiograph body generates the electrocardiogram on the basis of a lead signal sent by the active measurement electrodes.

17 Claims, 35 Drawing Sheets

(51) Int. Cl.
*A61B 5/30* (2021.01)
*A61B 5/00* (2006.01)

(52) U.S. Cl.
CPC ............ *A61B 5/339* (2021.01); *A61B 5/6804* (2013.01); *A61B 5/70* (2013.01)

(56) References Cited

U.S. PATENT DOCUMENTS

| | | | | |
|---|---|---|---|---|
| 5,511,553 | A * | 4/1996 | Segalowitz | A61B 5/412 |
| | | | | 128/903 |
| 6,441,747 | B1 | 8/2002 | Khair | |
| 6,496,705 | B1 * | 12/2002 | Ng | H04L 67/125 |
| | | | | 600/509 |
| 7,272,428 | B2 * | 9/2007 | Hopman | A61B 5/0006 |
| | | | | 600/382 |
| 7,670,295 | B2 * | 3/2010 | Sackner | G16H 40/67 |
| | | | | 600/595 |
| 7,881,778 | B2 * | 2/2011 | Rantala | A61B 5/301 |
| | | | | 600/509 |
| 7,996,056 | B2 * | 8/2011 | Rowlandson | A61N 1/0484 |
| | | | | 600/386 |
| 8,315,695 | B2 * | 11/2012 | Sebelius | A61B 5/0006 |
| | | | | 600/509 |
| 10,835,144 | B2 * | 11/2020 | Wei | A61B 5/291 |
| 2002/0045836 | A1 * | 4/2002 | Alkawwas | A61B 5/318 |
| | | | | 600/509 |
| 2002/0045837 | A1 * | 4/2002 | Wei | A61B 5/327 |
| | | | | 600/509 |
| 2002/0109621 | A1 * | 8/2002 | Khair | A61B 5/0006 |
| | | | | 340/870.07 |
| 2006/0025695 | A1 * | 2/2006 | Wei | A61B 5/327 |
| | | | | 600/509 |
| 2006/0047212 | A1 * | 3/2006 | Wei | A61B 5/327 |
| | | | | 600/509 |
| 2006/0235317 | A1 * | 10/2006 | Wei | A61B 5/318 |
| | | | | 600/509 |
| 2010/0234746 | A1 * | 9/2010 | Sebelius | A61B 5/0006 |
| | | | | 600/509 |
| 2011/0001497 | A1 * | 1/2011 | Chetelat | A61B 5/30 |
| | | | | 324/692 |
| 2012/0029371 | A1 * | 2/2012 | Wei | A61B 5/0006 |
| | | | | 600/509 |
| 2014/0228665 | A1 | 8/2014 | Albert | |
| 2015/0005585 | A1 * | 1/2015 | Xu | A61B 5/291 |
| | | | | 600/300 |
| 2017/0127968 | A1 | 5/2017 | Yoneda | |
| 2017/0251939 | A1 * | 9/2017 | Santala | A61B 5/301 |
| 2018/0035908 | A1 * | 2/2018 | Wei | A61B 5/6805 |
| 2018/0092563 | A1 * | 4/2018 | Matthiesen | A61B 5/6852 |
| 2019/0261927 | A1 * | 8/2019 | Matthiesen | A61B 5/349 |
| 2020/0405171 | A1 * | 12/2020 | Wei | A61B 5/339 |

FOREIGN PATENT DOCUMENTS

| | | |
|---|---|---|
| JP | 2004503266 A | 2/2004 |
| JP | 2012029904 A | 2/2012 |
| JP | 2016521164 A | 7/2016 |
| WO | 2016121337 A1 | 8/2016 |

* cited by examiner

Average Weight one measurement electrode falls off $$\begin{bmatrix} C1_{11} & C1_{12} & C1_{13} & C1_{14} & C1_{15} & C1_{16} & C1_{17} & C1_{18} \\ C1_{21} & C1_{22} & C1_{23} & C1_{24} & C1_{25} & C1_{26} & C1_{27} & C1_{28} \\ C1_{31} & C1_{32} & C1_{33} & C1_{34} & C1_{35} & C1_{36} & C1_{37} & C1_{38} \\ C1_{41} & C1_{42} & C1_{43} & C1_{44} & C1_{45} & C1_{46} & C1_{47} & C1_{48} \\ C1_{51} & C1_{52} & C1_{53} & C1_{54} & C1_{55} & C1_{56} & C1_{57} & C1_{58} \\ C1_{61} & C1_{62} & C1_{63} & C1_{64} & C1_{65} & C1_{66} & C1_{67} & C1_{68} \end{bmatrix}$$

two measurement electrodes fall off $$\begin{bmatrix} C2_{11} & C2_{12} & C2_{13} & C2_{14} & C2_{15} & C2_{16} & C2_{17} & C2_{18} \\ C2_{21} & C2_{22} & C2_{23} & C2_{24} & C2_{25} & C2_{26} & C2_{27} & C2_{28} \\ C2_{31} & C2_{32} & C2_{33} & C2_{34} & C2_{35} & C2_{36} & C2_{37} & C2_{38} \\ C2_{41} & C2_{42} & C2_{43} & C2_{44} & C2_{45} & C2_{46} & C2_{47} & C2_{48} \\ C2_{51} & C2_{52} & C2_{53} & C2_{54} & C2_{55} & C2_{56} & C2_{57} & C2_{58} \\ C2_{61} & C2_{62} & C2_{63} & C2_{64} & C2_{65} & C2_{66} & C2_{67} & C2_{68} \end{bmatrix}$$

three measurement electrodes fall off $$\begin{bmatrix} C3_{11} & C3_{12} & C3_{13} & C3_{14} & C3_{15} & C3_{16} & C3_{17} & C3_{18} \\ C3_{21} & C3_{22} & C3_{23} & C3_{24} & C3_{25} & C3_{26} & C3_{27} & C3_{28} \\ C3_{31} & C3_{32} & C3_{33} & C3_{34} & C3_{35} & C3_{36} & C3_{37} & C3_{38} \\ C3_{41} & C3_{42} & C3_{43} & C3_{44} & C3_{45} & C3_{46} & C3_{47} & C3_{48} \\ C3_{51} & C3_{52} & C3_{53} & C3_{54} & C3_{55} & C3_{56} & C3_{57} & C3_{58} \\ C3_{61} & C3_{62} & C3_{63} & C3_{64} & C3_{65} & C3_{66} & C3_{67} & C3_{68} \end{bmatrix}$$

When four through six measuring electrodes fall off, the value of n in C(n) above is 4, 5, or 6 and values are like above.

Average weight is by gender and age male 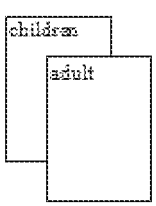 female 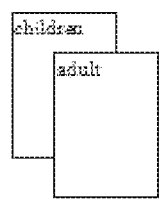

Fig. 9

Optimal Weight
(for a subject)

one measurement electrode falls off $$\begin{bmatrix} C1_{11} & C1_{1B} & C1_{11} & C1_{12} & C1_{13} & C1_{14} & C1_{15} & C1_{16} \\ C1_{21} & C1_{2B} & C1_{21} & C1_{22} & C1_{23} & C1_{24} & C1_{25} & C1_{26} \\ C1_{31} & C1_{3B} & C1_{31} & C1_{32} & C1_{33} & C1_{34} & C1_{35} & C1_{36} \\ C1_{41} & C1_{4B} & C1_{41} & C1_{42} & C1_{43} & C1_{44} & C1_{45} & C1_{46} \\ C1_{51} & C1_{5B} & C1_{51} & C1_{52} & C1_{53} & C1_{54} & C1_{55} & C1_{56} \\ C1_{81} & C1_{8B} & C1_{81} & C1_{82} & C1_{83} & C1_{84} & C1_{85} & C1_{86} \end{bmatrix}$$

two measurement electrodes fall off $$\begin{bmatrix} C2_{11} & C2_{1B} & C2_{11} & C2_{12} & C2_{13} & C2_{14} & C2_{15} & C2_{16} \\ C2_{21} & C2_{2B} & C2_{21} & C2_{22} & C2_{23} & C2_{24} & C2_{25} & C2_{26} \\ C2_{31} & C2_{3B} & C2_{31} & C2_{32} & C2_{33} & C2_{34} & C2_{35} & C2_{36} \\ C2_{41} & C2_{4B} & C2_{41} & C2_{42} & C2_{43} & C2_{44} & C2_{45} & C2_{46} \\ C2_{51} & C2_{5B} & C2_{51} & C2_{52} & C2_{53} & C2_{54} & C2_{55} & C2_{56} \\ C2_{81} & C2_{8B} & C2_{81} & C2_{82} & C2_{83} & C2_{84} & C2_{85} & C2_{86} \end{bmatrix}$$

three measurement electrodes fall off $$\begin{bmatrix} C3_{11} & C3_{1B} & C3_{11} & C3_{12} & C3_{13} & C3_{14} & C3_{15} & C3_{16} \\ C3_{21} & C3_{2B} & C3_{21} & C3_{22} & C3_{23} & C3_{24} & C3_{25} & C3_{26} \\ C3_{31} & C3_{3B} & C3_{31} & C3_{32} & C3_{33} & C3_{34} & C3_{35} & C3_{36} \\ C3_{41} & C3_{4B} & C3_{41} & C3_{42} & C3_{43} & C3_{44} & C3_{45} & C3_{46} \\ C3_{51} & C3_{5B} & C3_{51} & C3_{52} & C3_{53} & C3_{54} & C3_{55} & C3_{56} \\ C3_{81} & C3_{8B} & C3_{81} & C3_{82} & C3_{83} & C3_{84} & C3_{85} & C3_{86} \end{bmatrix}$$

When four through six measuring electrodes fall off, the value of n in C(n) above is 4, 5, or 6 and values are like above.

Fig. 10

ELECTROCARDIOGRAPH SYSTEM, ELECTROCARDIOGRAPHIC MEASUREMENT ELECTRODE, AND ELECTROCARDIOGRAPHIC MEASUREMENT METHOD

CROSS-REFERENCE TO RELATED APPLICATION

This application claims the benefit of international application number PCT/JP 2018/006257, filed on Feb. 21, 2018. The contents of this application are incorporated herein by reference in their entirety.

FIELD OF THE INVENTION

The present invention relates to an electrocardiograph system for taking an electrocardiogram (ECG), electrocardiographic measurement electrode used in the electrocardiograph system, and an electrocardiographic measurement method.

DESCRIPTION OF RELATED ARTS

A 12-lead ECG is widely used as an industry standard for ECG test. When taking a 12-lead ECG, a subject lies down on the bed, and the measurement electrodes are attached to the limbs at four positions on both arms and legs for detecting the limb leads, and to six predetermined positions on the chest for detecting chest leads, respectively.

As described above, in order to obtain the 12-lead ECG, a measurer needs to accurately attach the measurement electrodes to predetermined 10 positions on the body of the subject. A cable (usually long, thick and heavy) must be connected to each measurement electrode and an electrocardiograph body. For this reason, miniaturization of an electrocardiograph is limited so far. In addition, it is inconvenient to bring the electrocardiograph outside a hospital, and it is also troublesome to move the electrocardiograph from room to room within a hospital.

In addition, since it is troublesome for the measurer to handle the cables and it is difficult for the subject to place measurement electrodes for him/herself, the 12-lead ECG is usually only applicable to a medical institution such as a hospital so far. It is difficult to apply the 12-lead ECG for home medical care, etc.

In recent years, some compact and easy-to-use wireless electrocardiographs are developed. An example is disclosed in Patent document 1 below. However, the electrocardiographs is to record bipolar lead ECG, and is applied to monitor arrhythmia and the like. It cannot detect a 12-lead ECG and is not suitable for standard ECG diagnosis. No 12-lead electrocardiograph can be measured wirelessly by far.

PRIOR ART DOCUMENT

Patent Document

Patent Document 1 Japanese Patent Laid-Open No. 2015-20050

SUMMARY

The present invention is to provide a wireless electrocardiograph system, a wireless electrocardiographic measurement electrode, and a wireless electrocardiographic measurement method for a standard 12-lead ECG, a 12-lead ECG using Mason-Likar lead method, an ECG of body surface electrocardiographic mapping and alike, without utilizing a cable connection between measurement electrodes and a main body of electrocardiograph.

The electrocardiograph system according to the present invention for achieving the above object has a plurality of measurement electrodes, a Wilson terminal, and an electrocardiograph body. The measurement electrodes acquire the electrocardiographic signals of the subject. The plurality of measurement electrodes has active measurement electrodes that communicates with the electrocardiograph body by wireless communication, and passive measurement electrodes connected to active measurement electrodes and to the Wilson terminal. The Wilson terminal connecting to the measurement electrodes forms an indifferent electrode. The electrocardiograph body generates an ECG based on the lead signals transmitted by the active measurement electrodes.

The active measurement electrode and the passive measurement electrode are devices that integrate a patch electrode and a control-communication device. The control-communication device of the active measurement electrode wirelessly transmits the potential difference between the local electrocardiographic signal acquired by the patch electrode and the input signal from the input terminal. Another function of the control-communication device is to output the local electrocardiographic signal acquired by the patch electrode to the output terminal as it is. Unlike the control-communication device of the active measurement electrode, the control-communication device of the passive measurement electrode only has a function of outputting the local electrocardiographic signal acquired by the patch electrode to the output terminal as it is.

In the case of standard 12-lead ECG, the active measurement electrodes are attached to the left arm (LA) and left leg (LL), and the passive measurement electrodes are attached to the right arm (RA) and right leg (RL). The output terminal of RA is connected to the input terminal of LA, and the potential difference between LA and RA is wirelessly output to the electrocardiograph body as lead I of limb lead. The output terminal of RA is connected to the input terminal of LL, and the potential difference between RA and LL is wirelessly output to the electrocardiograph body as lead II of limb lead. Further, the output terminal of LA, LL, and RA are connected to the input terminal of the Wilson terminal to form the indifferent electrode. In addition, active measurement electrodes are attached to the chest lead, and the output terminal of the indifferent electrode is connected to the input terminals of the chest lead, respectively, and the potential differences between the induced potentials by chest electrodes and the indifferent electrode are wirelessly output to the electrocardiograph body as chest lead.

The measurement electrode according to the present invention for achieving the above object comprises a patch electrode and a control-communication device. The patch electrode is attached on the body surface for acquiring electrocardiographic signals of the body. The control-communication device processes the electrocardiographic signals (local electrocardiographic signals) acquired by the attached electrode.

The measurement electrode according to the present invention for achieving the above object comprises active measurement electrodes and passive measurement electrodes. The control-communication device of the active measurement electrode has two functions. One is to wirelessly transmit the potential difference between the local electrocardiographic signal acquired by the patch electrode and the input signal from the input terminal. The other is to output the local electrocardiographic signal acquired by the patch electrode to the output terminal as it is. The control-communication device of the passive measurement electrode only comprises a function of outputting the local electrocardiographic signal acquired by the patch electrode to the output terminal as it is. The control-communication device of active measurement electrode consists of an input terminal, an ECG generator, and a wireless transmitter. The input terminal inputs the electrocardiographic signals from the patch electrode and the outside. The ECG generator generates a lead signal using the input electrocardiographic signals. The wireless transmitter transmits the generated lead signal to the outside by wireless communication. The control-communication device of passive measurement electrode has an input terminal and an output terminal. The input terminal and the output terminal are electrically connected, and the electrocardiographic signals input from the input terminal is output to the output terminal.

Furthermore, the electrocardiographic measurement method according to the present invention for achieving the above object includes: a step of acquiring electrocardiographic signals from the subject's chest and limbs of a subject, a step of generating an potential of an indifferent electrode from the electrocardiographic signals of the right arm, left arm, and left leg out of the electrocardiographic signals of the subject's limbs, a step of wirelessly transmitting chest lead signals obtained from the potentials of the chest electrocardiographic signals and the potential of the indifferent electrode, a step of wirelessly transmitting the limb lead signals from the potential of the electrocardiographic signals of the limb, and a step of generating an electrocardiogram based on the transmitted chest lead signals and limb lead signals.

Furthermore, the electrocardiographic measurement method according to the present invention for achieving the above object includes:

a step of acquiring electrocardiographic signals from a subject's chest and limbs, a step of generating the electric potential reference of an indifferent electrode from the electrocardiographic signals of the right supraclavicle, the left subclavicle, the left anterior iliac spine or left lower rib arch among the electrocardiographic signals of limbs of the subject, a step of wirelessly transmitting chest lead signals obtained from the potentials of the chest electrocardiographic signals and the electric potential reference of the indifferent electrode, a step of wirelessly transmitting the limb lead signals from the potential of the electrocardiographic signals of the limbs, and a step of generating an electrocardiogram based on the transmitted chest lead signals and limb leads signals.

According to the electrocardiograph system, the electrocardiographic measurement electrode, and the electrocardiographic measurement method according to the present invention, in an electrocardiograph that requires a large number of unipolar leads on the body surface, such as a 12-lead electrocardiogram, the acquired body surface cardiac potentials can be converted into lead signals necessary for an ECG and transmitted to the main body of the electrocardiograph by wireless communication. As a result, it is no longer necessary to connect a cable between the measurement electrodes and the electrocardiograph body, and the placement of the measurement electrodes is improved so that the ECG test for a subject becomes much easier than ever before, and the ECG applications are made more widely than ever before.

BRIEF DESCRIPTION OF THE DRAWINGS

FIG. 9 is an example of an average weight stored by an average weight database. (first embodiment).

FIG. 10 is an example of an optimal weight stored by an optimal weight database. (first embodiment).

DETAILED DESCRIPTION OF EMBODIMENTS

Next, the electrocardiograph system, electrocardiographic measurement electrode and electrocardiographic measurement method of the invention are described in detail from first embodiment to eighth embodiment, referring to the attached drawings.

First Embodiment (Overall Configuration of Electrocardiograph System)

Figure 1:
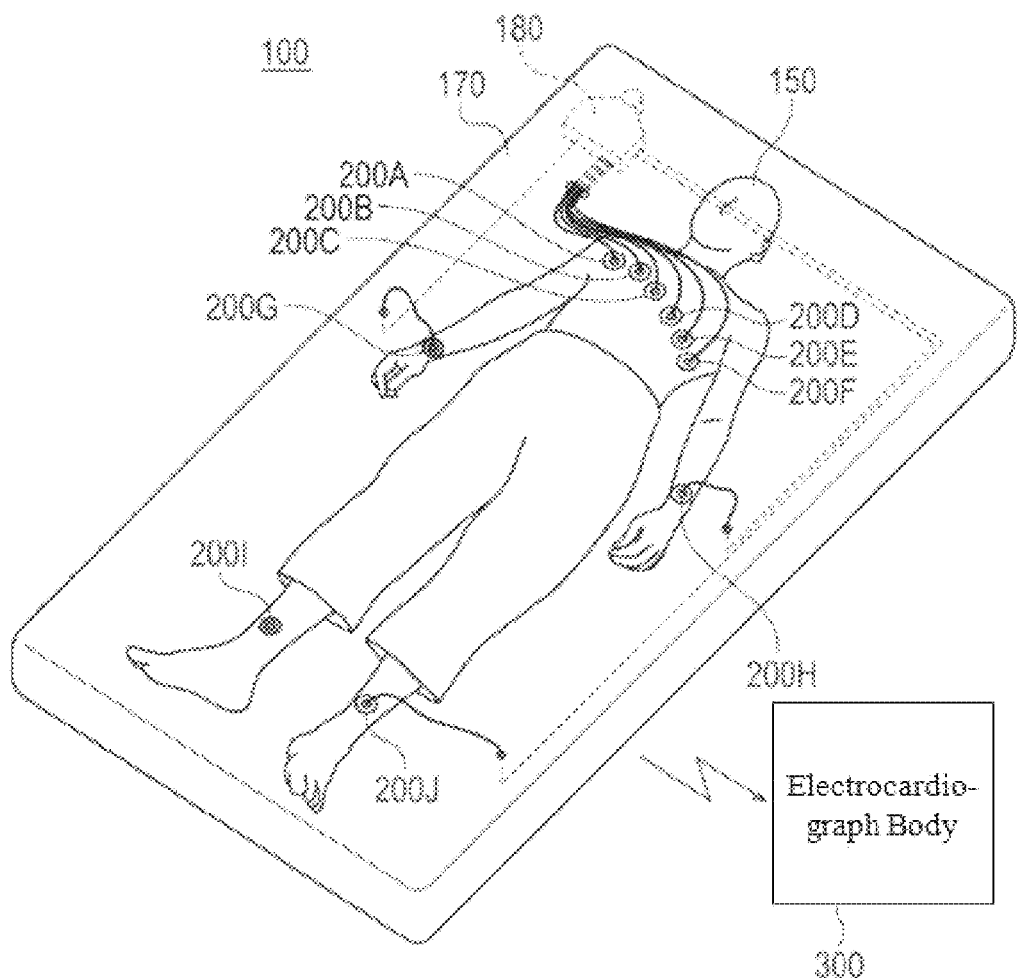
FIG. 1 is a structure diagram of an electrocardiograph system. (first embodiment).

FIG. 1 is a structure diagram of the electrocardiograph system of first embodiment. The description of the first embodiment takes the acquisition of a 12-lead ECG as an example.

As shown in FIG. 1, when acquiring the 12-lead ECG in the electrocardiograph system 100 of the first embodiment, firstly, subject 150 is lying in bed 170. Then, the active measurement electrodes 200H, 200J, passive measurement electrodes 200G, 200I are used to acquire the electrocardiographic signals of the limbs of the subject 150 by attaching the electrodes at four places of the arms and legs of the subject 150. Further, at 6 places of the chest of the subject 150, the active measurement electrodes 200A, 200B, 200C, 200D, 200E and 200F for acquiring electrocardiographic signals of the chest of the subject 150 are attached. In addition, a Wilson terminal 180 is provided which is connected to the passive measurement electrode 200G and the active measurement electrode 200H and 200J attached to the right arm, left arm, and left leg of the subject 150, respectively, to form an indifferent electrode. The Wilson terminal 180 is arranged under the bed 170 to prevent hindering the measurement. The passive measurement electrodes 200G, active measurement electrodes 200H and 200J are connected to the input terminals of Wilson terminal 180, and the active measurement electrodes 200A, 200B, 200C, 200D, 200E and 200F are connected to the output terminals of Wilson terminal 180. The input terminals of Wilson terminal 180 are connected to the passive measurement electrode 200G, the active measurement electrode 200H and 200J through the cables, which are also configured under the bed 170 to prevent hindering the measurement. In FIG. 1, these cables arranged under the bed 170 are shown in dashed lines.

The active measurement electrodes 200H and 200J transmit lead signals obtained from the potentials of electrocardiographic signals of limbs obtained from passive measurement electrodes 200G, 200I and active measurement electrodes 200H and 200J through wireless communication. Also, differing from active measurement electrodes 200H and 200J, passive measurement electrodes 200G and 200I do not have the function of transmitting lead signals through wireless communication. In addition, the active measurement electrodes 200A, 200B, 200C, 200D, 200E and 200F transmit the lead signals obtained from the potential difference of the electrocardiographic signal obtained from the active measurement electrode 200A, 200B, 200C, 200D, 200E, 200F and the indifferent electrode of the Wilson terminal 180. Electrocardiograph body 300 generates ECGs based on lead signals sent by active measurement electrodes 200A, 200B, 200C, 200D, 200E, 200F, 200H and 200J.

(Configuration of Measurement Electrode)

Figure 2A:
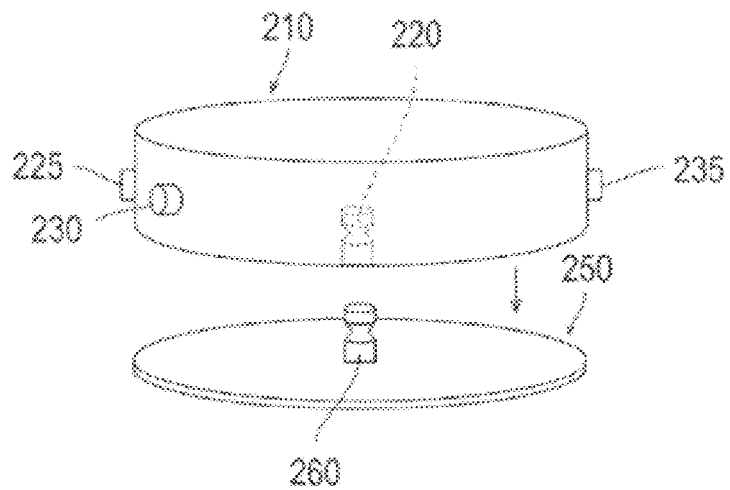
FIG. 2A is an external view of an active measurement electrode. (first embodiment).

FIG. 2A is an external view of active measurement electrodes 200A, 200B, 200C, 200D, 200E, 200F, 200H and 200J.

The active measurement electrodes 200A-200F have a patch electrode 250 attached on the chest of the subject 150 to obtain the local electrocardiographic signals of the subject 150's chest, and a control-communication device 210 for processing the local electrocardiographic signal acquired from the patch electrode 250. The active measurement electrodes 200H and 200J have a patch electrode 250 attached to the left arm and left leg of the subject 150 to acquire local electrocardiographic signals of the limbs of the subject 150; and a control-communication device 210 for processing the local electrocardiographic signal obtained from the patch electrode 250. The patch electrode 250 is placed on the left arm and left leg of the examinee 150 to obtain the local electrocardiographic signal of the limbs of the subject 150.

The control-communication device 210 has a concave input terminal 220 for inputting a local electrocardiographic signal from the patch electrode 250 and an input terminal 225 for inputting an external electrocardiographic signal. The patch electrode 250 has a convex connector 260 which electrically connects the input terminal 220 of the control-communication device 210. The concave shape of the input terminal 220 and the convex shape of the connector 260 have the same shape so that they can be fitted by one touch. The convex connector 260 is inserted into the concave input terminal 220 to make it chimeric, so as to ensure the solid mechanical and electrical connection between the input terminal 220 and the connector 260, and to achieve the integration of the patch electrode 250 and the control-communication device 210. The input terminal 225 arranged on the peripheral part of the control-communication device 210 is cylindrical in shape, to input the electrocardiographic signal from Wilson terminal 180 (refer to FIG. 1). The input terminal 225 is connected to a signal line from the Wilson terminal 180. The cables are connected in a one-touch manner through connectors such as plugs or clips. In addition, the connector is not limited to plugs or clips.

The control-communication device 210 has an output terminal 230 which outputs an electrocardiographic signal input from the connector 260 to the outside. In addition, the control-communication device 210 has a grounding terminal 235 connected with the output terminal of other control communication-devices 210. The output terminal 230 and the grounding terminal 235 are arranged on the peripheral part of the control-communication device 210, and have a cylindrical shape similar to the input terminal 225. In addition, in the present embodiment, the output terminal 230 and the grounding terminal 235 are cylindrical in shape, and of course they can be other shapes.

Figure 2B:
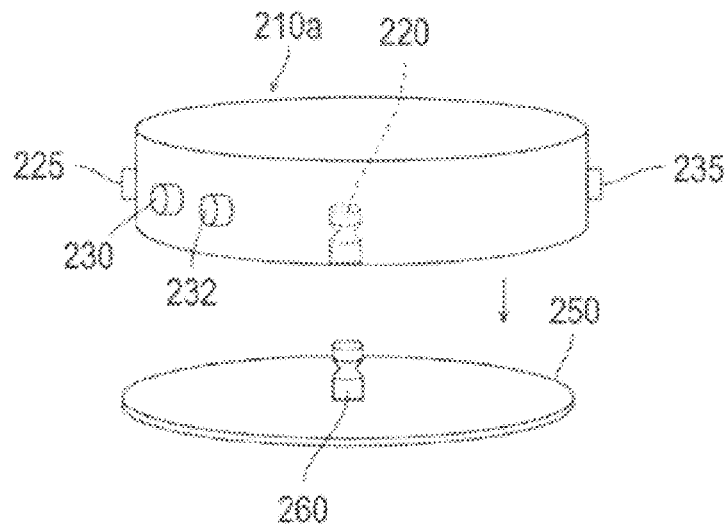
FIG. 2B is an external view of a passive measurement electrode. (first embodiment).

FIG. 2B is an external view of passive measurement electrodes 200G and 200I. The passive measurement electrodes 200G and 200I have a patch electrode 250 for acquiring the electrocardiographic signals of the subject 150 and a control-communication device 210a for processing the electrocardiographic signals obtained from the patch electrode 250. Passive measurement electrodes 200G and 200I are placed on the right arm and the right leg of the subject 150 (refer to FIG. 1).

The output terminal 230 is a terminal for outputting a local electrocardiographic signal from the input terminal 220 to other active measurement electrodes 200H, 200J. In addition, the output terminal 232 is a terminal for outputting a local electrocardiographic signal from the input terminal 220 to the Wilson terminal 180 (see FIG. 1). Signal lines are used respectively to connect the output terminal 230 and the output terminals of other active measurement electrodes 200H, 200J, and connect the output terminal 232 and the Wilson terminal 180. The signal line is connected by plugs or clips, but the connector is not limited to plugs or clips.

The control-communication device 210a has an output terminal 232 which is not provided in the control-communication device 210. The output terminal 232 is arranged at the peripheral part of the control-communication device 210a, and have a cylindrical shape similar to the output terminal 230. In addition, though the output terminal 232 is cylindrical, it can also be of other shapes.

(Configuration of Patch Electrode)

Figure 3A:
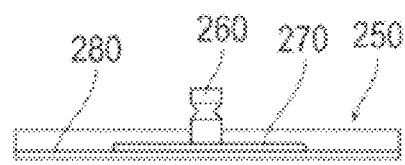
FIG. 3A is a side view of the patch electrodes constituting the active and passive measurement electrode. (first embodiment).
Figure 3B:
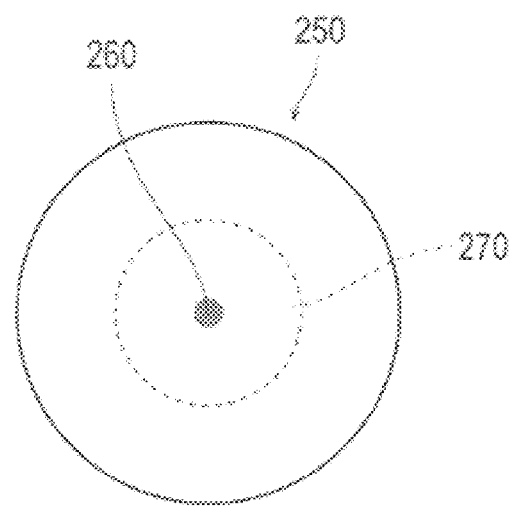
FIG. 3B is a bottom view of the patch electrodes constituting the active and passive measurement electrode. (first embodiment).

FIG. 3A is a side view of a patch electrode forming an active or passive measurement electrode. FIG. 3B is a bottom view of a patch electrode forming an active or passive measurement electrode.

As shown in FIGS. 3A and 3B, the patch electrode 250 has a convex connector 260 that electrically connects the concave input terminals 220 of the control-communication devices 210 and 210a (see FIGS. 2A and 2B), an electrode plate 270 which is attached to one end of the connector 260, and a conductive gel 280 having an adhesive property which is formed on the surface of the electrode plate 270. Also, the conductive gel 280 preferably has high adhesiveness and good conductivity.

The patch electrode 250 is attached by bringing the surface on which the conductive gel 280 is formed into close contact with the body surface of the subject 150. An electrocardiographic signal from the subject 150 is transmitted to the connector 260 via the conductive gel 280 and the electrode plate 270.

(Configuration of Control-Communication Device)

Figure 4:
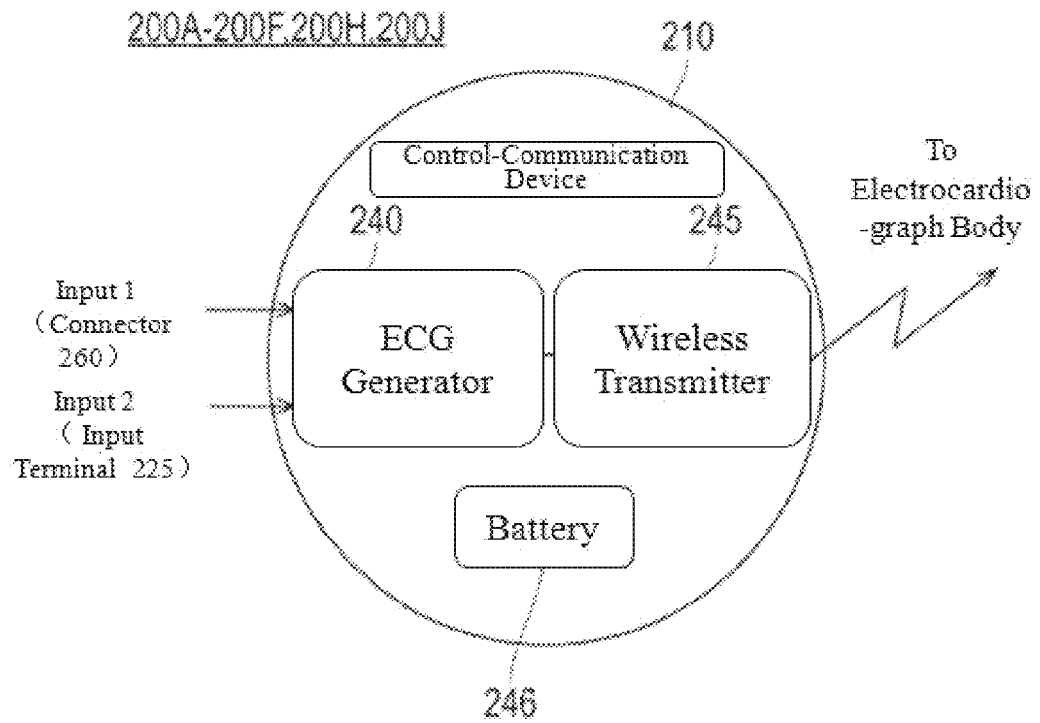
FIG. 4 is a block diagram of a control-communication device constituting an active measurement electrode. (first embodiment).

FIG. 4 is a block diagram of a control-communication device that constitutes an active measurement electrode.

The control-communication device 210 forming the active measurement electrodes 200A-200F, 200H, 200J has an ECG generator 240 and a wireless transmitter 245. The ECG generator 240 generates an electrocardiographic lead signal using the electrocardiographic signal input from the connector 260 of the patch electrode 250 and the input terminal 225 of the control-communication device 210.

Specifically, the local electrocardiographic signal acquired by the patch electrode 250 is input from the input 1, and the electrocardiographic signal from the Wilson terminal 180 is input from the input 2. The ECG generator 240 processes these electrocardiographic signals to generate lead signals.

The wireless transmitter 245 transmits the lead signal generated by the ECG generator 240 to the outside by wireless communication. The wireless communication used when the wireless transmitter 245 transmits the lead signal to the outside is performed by any one of radio waves, infrared rays, wireless LAN (Wi-Fi), and Bluetooth (registered trademark). The control-communication device 210 includes a battery 246, and the ECG generator 240 and the wireless transmitter 245 operate on the power of the battery 246.

In addition, though the passive measurement electrodes 200G and 200I have the control-communication device 210a, the control-communication device 210a does not have the ECG generator 240 and the wireless transmitter 245. This is because the passive measurement electrode 200G need only output the electrocardiographic signal input by the passive measurement electrode 200G itself to the active measurement electrodes 200H and 200J and the Wilson terminal 180. Further, the passive measurement electrode 200I only needs to output the local electrocardiographic signal input by itself to the active measurement electrodes 200A-200F, 200H, and 200J.

(Configuration of ECG Generator)

Figure 5:
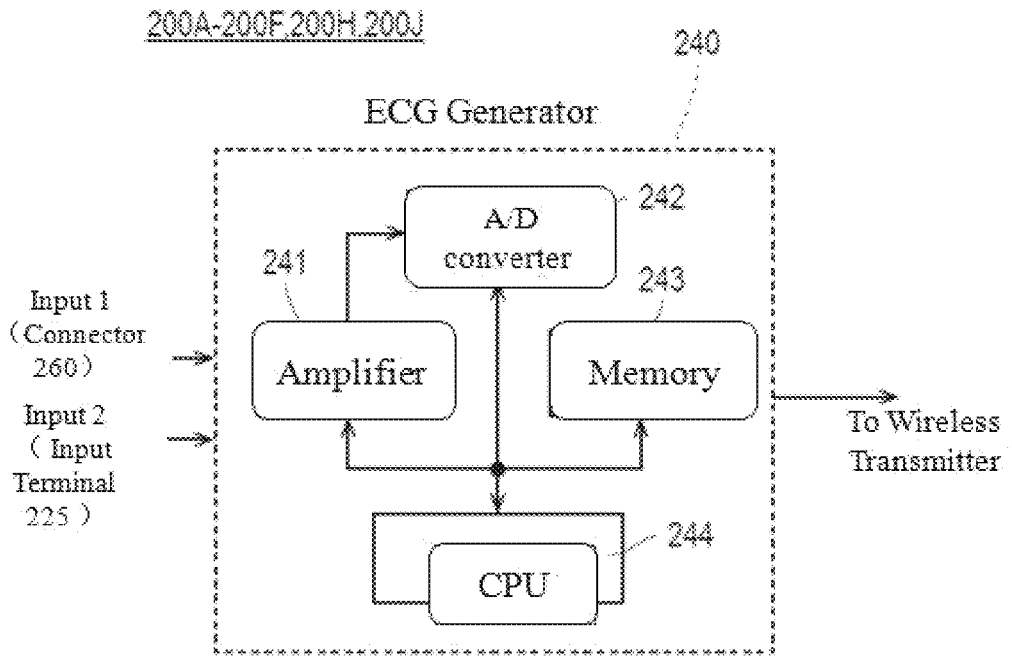
FIG. 5 is a block diagram of the ECG generator shown in FIG. 4. (first embodiment).

FIG. 5 is a block diagram of the ECG generator shown in FIG. 4

The ECG generator 240 has an amplifier 241, an A/D converter 242, a memory 243, and a CPU 244. The amplifier 241 amplifies the electrocardiographic signal input from the connector 260 (input 1) of the patch electrode 250 and the input terminal 225 (input 2) of the control-communication device 210. The A/D converter 242 converts the electrocardiographic signal amplified by the amplifier 241 into a digital signal. The memory 243 stores the electrocardiographic signal converted into a digital signal by the A/D converter 242. The CPU 244 calculates the lead signal using the electrocardiographic signal that has been converted into a digital signal. The calculated lead signal is output to the wireless transmitter 245 shown in FIG. 4.

(Operation of Measurement Electrode)

Figure 6:
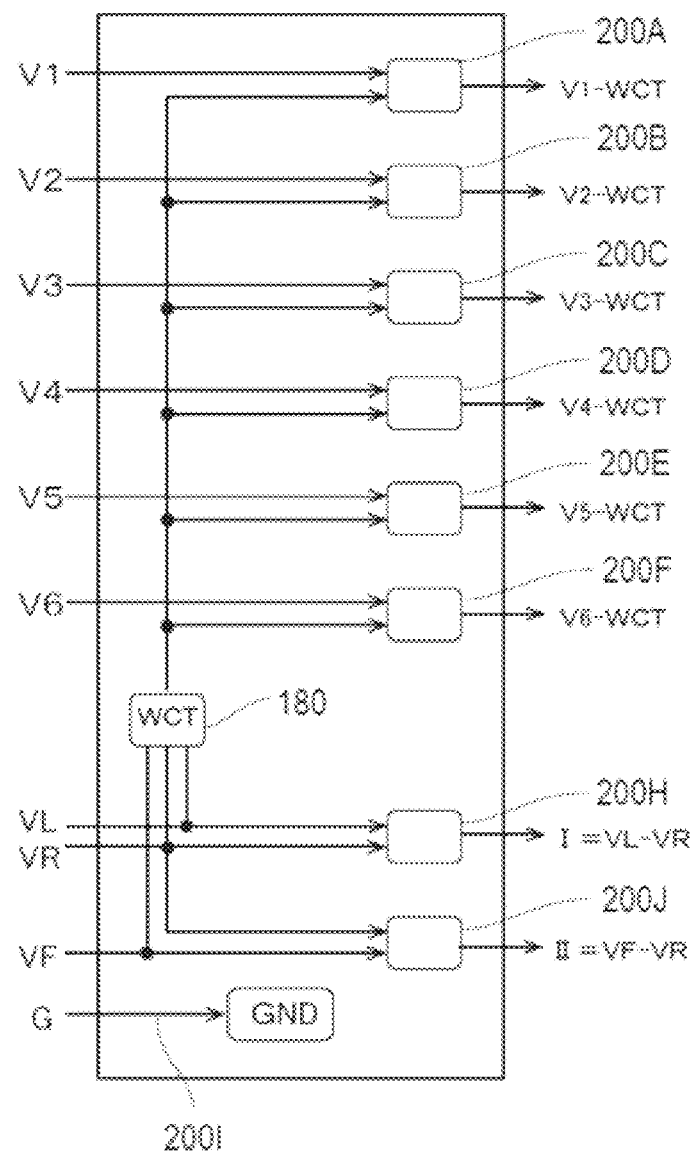
FIG. 6 is a connection diagram of the active and passive measurement electrodes of the electrocardiograph system of FIG. 1. (first embodiment).

FIG. 6 is a connection diagram of active and passive measurement electrodes that configure the electrocardiograph system 100 of FIG. 1. First, active measurement electrodes 200A-200F operate as follows.

The active measurement electrode 200A inputs the potential V1 of the local electrocardiographic signal from the patch electrode 250 (see FIG. 2A) of the active measurement electrode 200A via the connector 260. Further, the potential WCT of the electrocardiographic signal output from the Wilson terminal 180 is input from the input terminal 225 of the active measurement electrode 200A.

Here, the potential WCT of the electrocardiographic signal output by the Wilson terminal 180 is the sum of the potential VR of the electrocardiographic signal obtained by the right arm passive measurement electrode 200G, the potential VL of the electrocardiographic signal obtained by the left arm active measurement electrode 200H, and the potential VF of the electrocardiographic signal obtained by the left leg active measurement electrode 200J, divided by 3, that is the value of (VR+VL+VF)/3. The active measurement electrode 200A calculates V1-WCT and sends the result wirelessly as a chest lead signal.

Similarly, the active measurement electrode 200B inputs the potential V2 of the local electrocardiographic signal from the patch electrode 250 of the active measurement electrode 200B via the connector 260. Further, the potential WCT of the electrocardiographic signal output from the Wilson terminal 180 is input from the input terminal 225 of the active measurement electrode 200B. The active measurement electrode 200B calculates V2-WCT and wirelessly transmits the result as a chest lead signal.

Similarly, the active measurement electrode 200C calculates V3-WCT and wirelessly transmits the result as a chest lead signal. The active measurement electrode 200D calculates V4-WCT and wirelessly transmits the result as a chest lead signal. The active measurement electrode 200E calculates V5-WCT and wirelessly transmits the result as a chest lead signal. The active measurement electrode 200F calculates V6-WCT and wirelessly transmits the result as a chest lead signal.

Then, the passive measurement electrodes 200G and 200I, the active measurement electrodes 200H and 200J operate as follows.

The passive measurement electrode 200G inputs the potential VR of the local electrocardiographic signal from the patch electrode 250 (refer to FIG. 2B) of the passive measurement electrode 200G through the connector 260. The output terminal 230 of the passive measurement electrode 200G outputs the potential VR of the local electrocardiographic signal to the active measurement electrode 200H and the active measurement electrode 200J. In addition, the output terminal 232 outputs the potential VR of the local electrocardiographic signal to the Wilson terminal 180.

The active measurement electrode 200H receives the potential VL of the local electrocardiographic signal from the patch electrode 250 of the active measurement electrode 200H via the connector 260. The potential VR of the electrocardiographic signal output by the passive measurement electrode 200G is input from the input terminal 225 of the active measurement electrode 200H. The active measurement electrode 200H calculates VL−VR and sends the result wirelessly as the lead I of the limb leads. In addition, the potential VL of the electrocardiographic signal is output from the output terminal 232 to the Wilson terminal 180.

In addition, the passive measurement electrode 200I inputs the potential G of the local electrocardiographic signal from the patch electrode 250 of the passive measurement electrode 200I via the connector 260. This potential G becomes the ground of the circuit in the control-communication device 210 of the active measurement electrodes 200A-200F, 200H, and 200J and the control-communication device 201*a* of the passive measurement electrode 200G. Therefore, the output terminals 230, 232 of the passive measurement electrode 200I are connected to the active measurement electrodes 200A-200F, 200H, 200J and the ground terminal 235 of the passive measurement electrode 200G.

The active measurement electrode 200J inputs the potential VF of the local electrocardiographic signal from the patch electrode 250 of the active measurement electrode 200J via the connector 260. The potential VR of the electrocardiographic signal output by the passive measurement electrode 200G is input from the input terminal 225 of the active measurement electrode 200J. The active measurement electrode 200J calculates the VF−VR, and sends the result wirelessly as the lead II of the limb leads. In addition, the potential VF of the electrocardiographic signal is output from the output terminal 232 to the Wilson terminal 180.

(Configuration of Electrocardiograph Body)

Figure 7:
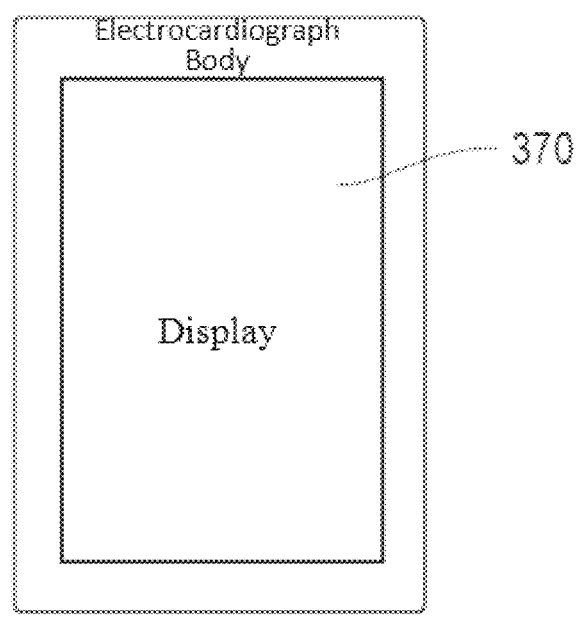
FIG. 7 is an external view of an electrocardiograph body. (first embodiment).

FIG. 7 is an external view of an electrocardiograph body. The electrocardiograph body 300 is a rectangular thin computer. Inside the electrocardiograph body 300, there is a control system for generating an electrocardiogram (ECG) based on the chest lead signal and the limb lead signal transmitted from the active measurement electrodes 200A-200F, 200H, and 200J. A display 370 for displaying the generated electrocardiogram or body surface mapping electrocardiogram is provided outside the electrocardiograph body 300.

Figure 8:
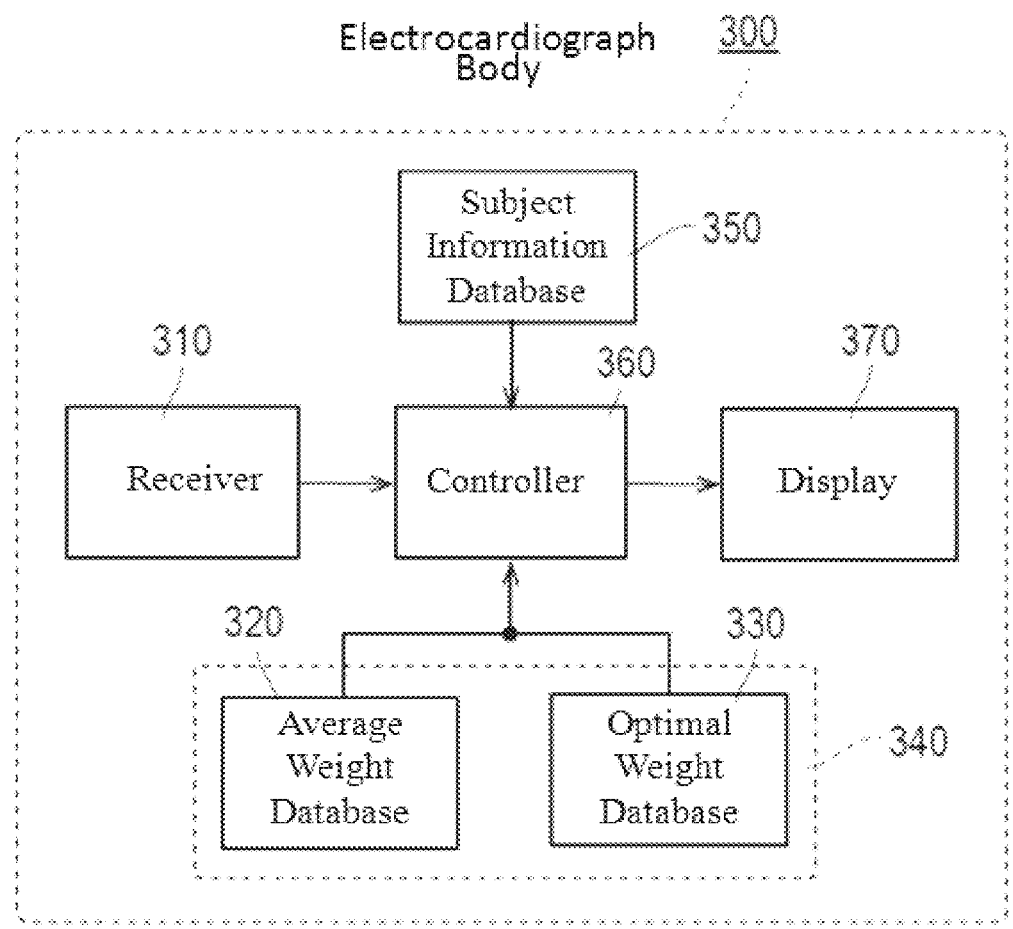
FIG. 8 is a block diagram of a control system of an electrocardiograph body. (first embodiment).

FIG. 8 is a block diagram of a control system of the electrocardiograph body 300. The electrocardiograph body 300 includes a receiver 310, an average weight database 320, an optimum weight database 330, a subject information database 350, a controller 360, and a display 370. The average weight database 320 and the optimum weight database 330 form a fall-off lead weight database 340.

The receiver 310 receives chest leads (V1-WCT, V2-WCT, V3-WCT, V4-WCT, V5-WCT, V6-WCT) and limb leads (Lead I, lead II) transmitted by the active measurement electrodes 200A-200F, 200H, and 200J.

Average weight database 320 stores the average weight obtained from an unspecified large number of subjects in consideration of the fact that any one of the active measurement electrodes 200A-200F falls off from the subject 150. A general formula for obtaining the electrocardiographic potential Vi of a fall-off electrode of any active measurement electrode 200A-200F is shown as bellow.

$$Vi = \sum_{j \neq i} c_{i,j}^{(n)} V_j \qquad \text{[Formula 1]}$$

Here, $C^{(n)}_{i,j}$ refers to weight, and $V_j$ is the potential of the active electrode j.

When making a 12-lead ECG, as shown in FIG. 1, it is necessary to detect the electrocardiographic potentials from a total of 10 measurement electrodes, including active measurement electrodes 200A-200F, 200H, 200J, and passive measurement electrodes 200G, 200I.

However, if an active measurement electrode falls off, such as 200C, the electrocardiographic potential cannot be obtained from the active measurement electrode 200C. Therefore, the above formula 1 can be used to obtain the electrocardiographic potential that would be measured from the active measurement electrode 200C if the 200C does not fall off.

Specifically, for example, the electrocardiographic potential V3 of the active measurement electrode 200C can be obtained by the following formula.

when active measurement electrode 200C falls off.

$$V_3 = C_{3I}{}^1 V_I + C_{3H}{}^1 V_H + C_{31}{}^1 V_1 + C_{32}{}^1 V_2 + C_{34}{}^1 V_4 \qquad \text{[Formula 2]}$$

When two active measurement electrodes, such as 200C and 200E, fall off, the electrocardiographic potential V3 of the active measurement electrode 200C and the electrocardiographic potential V5 of the active measurement electrode 200E can be obtained by the following formula.

When active measurement electrodes 200C and 200E fall off.

$$V_3 = C_{3I}{}^2 V_I + C_{3H}{}^2 V_H + C_{31}{}^2 V_1 + C_{32}{}^2 V_2 + C_{34}{}^2 V_4 + C_{36}{}^2 V_6$$

$$V_5 = C_{5I}{}^2 V_I + C_{5H}{}^2 V_H + C_{51}{}^2 V_1 + C_{52}{}^2 V_2 + C_{54}{}^2 V_4 + C_{56}{}^2 V_6 \qquad \text{[Formula 3]}$$

In this way, in order to obtain the potential of the measurement electrode that has fallen off from the potential of the measurement electrode other than the fall-off measurement electrode, the average weight database 320 includes a table storing the weights shown in FIG. 9. As shown in the figure, the average weight includes the weight when one measurement electrode falls off, the weight when two measurement electrodes fall off, and the weight when three measurement electrodes fall off, and the weight until all the electrodes of the six measurement electrodes of the chest fall off. In addition, if any measurement electrode of the limbs fall off, it is prompted to re-test.

The average weight database 320 stores the average weight shown in FIG. 9 applicable to all subjects, or store it separately by, for example, age and gender. When stored by age and gender, for example, it needs to be stored in a way that is divided into male children, male adults, female children, and female adults. The value of each average weight is obtained through actual measurement.

The optimal weight database 330 considers the case when any of the active measurement electrodes 200A to 200F falls off from the subject 150, and stores the optimal weight obtained from the subject him/herself.

The optimal weight is used in the same way as the average weight. The optimal weight is only applicable to the subject him/herself. As shown in FIG. 10, the optimal weight includes the weight when one measurement electrode falls off, the weight when two measurement electrodes fall off, the weight when three measurement electrodes fall off, etc. up to six, all the measurement electrodes on the chest fall off from the subject. In addition, if any measurement electrode of the limbs fall off, it is prompted to re-test.

The subject information database 350 stores subject information of the subject 150 such as patient name, age, and gender, at least.

Based on the lead signal received by the receiver 310, the controller 360 generates an electrocardiogram of the subject using the optimal weight if there is an optimal weight obtained from the subject 150 in the optimal weight database 330. On the other hand, if the optimal weight obtained from the subject 150 is not in the optimal weight storage database 330, the average weight in the average weight storage database 320 is used to generate the electrocardiogram of the subject 150.

The controller 360 identifies whether any of the active measurement electrodes 200A-200F falls off from the subject 150 through the lead signals received from the receiver 310. The controller 360 takes out the average weight or optimal weight corresponding to the fall-off state from the average weight database 320 or the optimal weight database 330.

The controller 360 takes out the optimal weight of the subject 150 from the optimal weight database 330 or the average weight suitable for the subject 150 from the average weight database 320 with reference to the subject information stored in the subject information database 350.

In addition, in first embodiment, the ECG generated by the controller 360 can be applied to any one of 12-lead ECG, 4-lead ECG, 3-lead ECG and body surface mapping ECG, but not limited to these ECGs.

The display 370 displays an ECG or a body surface mapping ECG generated by the controller 360.

(Operation of Electrocardiograph Body)

Figure 11:
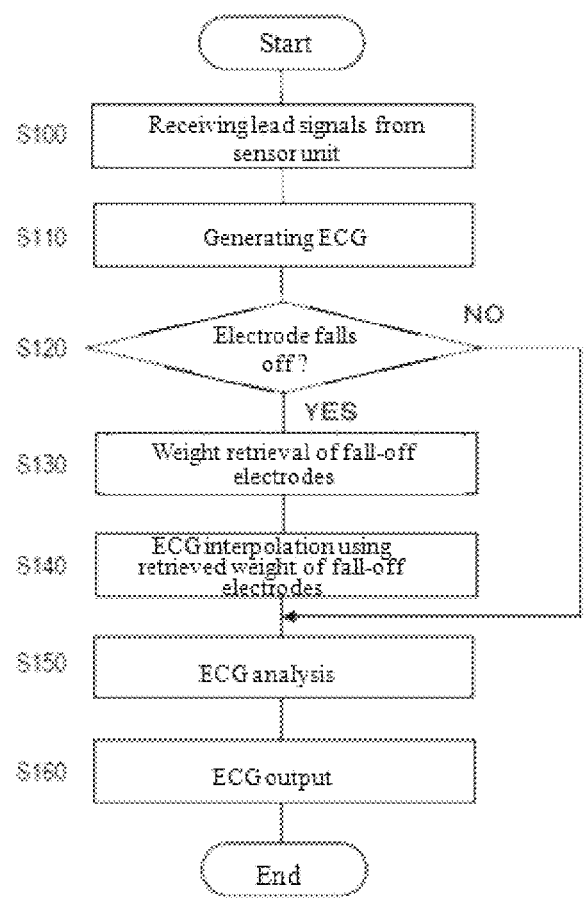
FIG. 11 is the operation flow chart of the controller of an electrocardiograph body. (first embodiment).

FIG. 11 is an operation flow diagram of the controller 360 of the electrocardiograph body 300.

The receiver 310 receives the lead signal (S100) transmitted from the control-communication devices 210 of the active measurement electrodes 200A-200F, 200H, 200J placed on the subject 150. The controller 360 generates an electrocardiogram (S110) of the measured subject 150 using the lead signals received by the receiver 310. The ECG generated at this time is a 12-lead ECG. The 12-lead ECG is generated by a common procedure as described below.

Specifically, as shown in FIG. 1, the active measurement electrodes 200A-200F output chest lead signals. Also, the active measurement electrodes 200H and 200J output limb lead signals.

That is, the following lead signals of the chest and limbs required for the generation of the electrocardiogram are output from the control-communication device 210.

Lead VI: $V1-(VR+VL+VF)/3$
Lead V2: $V2-(VR+VL+VF)/3$
Lead V3: $V3-(VR+VL+VF)/3$
Lead V4: $V4-(VR+VL+VF)/3$
Lead V5: $V5-(VR+VL+VF)/3$
Lead V6: $V6-(VR+VL+VF)/3$
Lead I: $VL-VR$
Lead II: $VF-VR$ Here, VR, VL and VF are electrocardiographic potentials on right hand, left hand and left leg respectively, and V1-V6 are electrocardiographic potentials on corresponding chest lead positions.

The generation of the 12-lead ECG also requires the following lead signals, which are obtained by the controller 360 through the following calculation.

Lead III: $II-I$
Lead aVR: $-(I+II)/2$
Lead aVL: $I-II/2$
Lead aVF: $II-I/2$

The controller 360 identifies whether there are electrodes 200A-200F that have fallen off from the subject 150 (S120). This identification is based on whether the lead signal of the chest from the active measurement electrode 200A-200F is normally input into the controller 360.

If a chest lead signal is not normally input from any of all active measurement electrodes 200A-200F, it is judged that there is a fall-off measurement electrode (S120: Yes). The controller 360 retrieves the weight of the fall-off lead (average or optimal weight) (S130) from the weight database 340 (refer to FIG. 8). The weight of a fall-off lead refers to the weight of interpolating the fall-off lead, for example, in the case where the measurement electrode has fallen off from the subject 150. The weight is not only a set for single electrode fall off, but also for various combinations of more electrodes falling off simultaneously. The processing of S130 will be described in detail later.

The controller 360 interpolates the ECG generated in the step of S110 by using the weight of the fall-off lead taken from the fall-off weight database 340 (S140). Through this interpolation, a more correct electrocardiogram is obtained. On the other hand, when all the active measurement electrodes 200A-200F do not fall off (S120: NO), the process proceeds directly to S150 without interpolation.

Next, the controller 360 analyzes the generated ECG (S150) and outputs the ECG to the display 370 (S160).

In this way, in the electrocardiograph system 100 of first embodiment, the correct ECG can be acquired even if when anyone of the measurement electrodes 200a-200f falls off.

Figure 12:
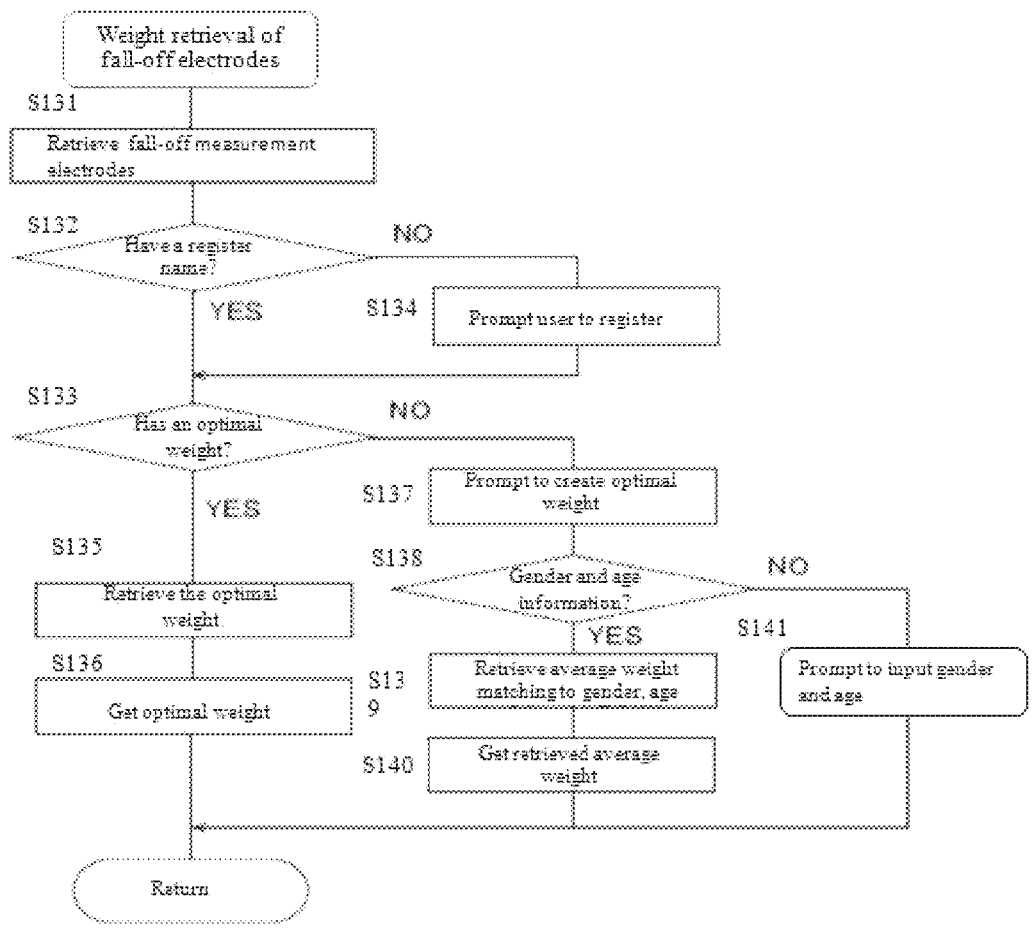
FIG. 12 is a flow chart showing the processing steps of retrieval of weight for fall-off leads. (first embodiment).

FIG. 12 is a flow chart showing the process step of search for weight of fall-off leads. The flow chart is a subroutine of step S130 in the flowchart of FIG. 11.

The controller 360 searches for which one of the active measurement electrodes 200A-200F is the fall-off measurement electrode based on the input chest lead signals and limb lead signals (S131), Then, it determines whether or not the personal name of the subject 150 has been input (S132). If there is a matching personal name (S132: Yes), it determines whether the optimal weight corresponding to the personal name exists in the optimal weight database 330 (S133). If there is no matching personal name (S132: No), the measurer who operates the system is prompted to register the subject as a user (S134).

If there is an optimal weight (S133: Yes), the controller 360 retrieves the optimal weight (S135) from the optimal weight database 330 and obtains the optimal weight (S136).

If there is no optimal weight (S133: no), the controller 360 prompts the measurer to create the optimal weight of the subject (S137). Next, the controller 360 determines whether the gender and age of the subject are stored in the subject information database 350 (S138). If the gender and age of the subject are stored (S138: Yes), the average weight consistent with the subject's gender and age is retrieved (S139) and the average weight is obtained (S140). On the other hand, if the gender and age of the subject are not stored in the subject information database 350 (S138: No), a prompt is given to the measurer to input the gender and age of the subject (S141).

Figure 13:
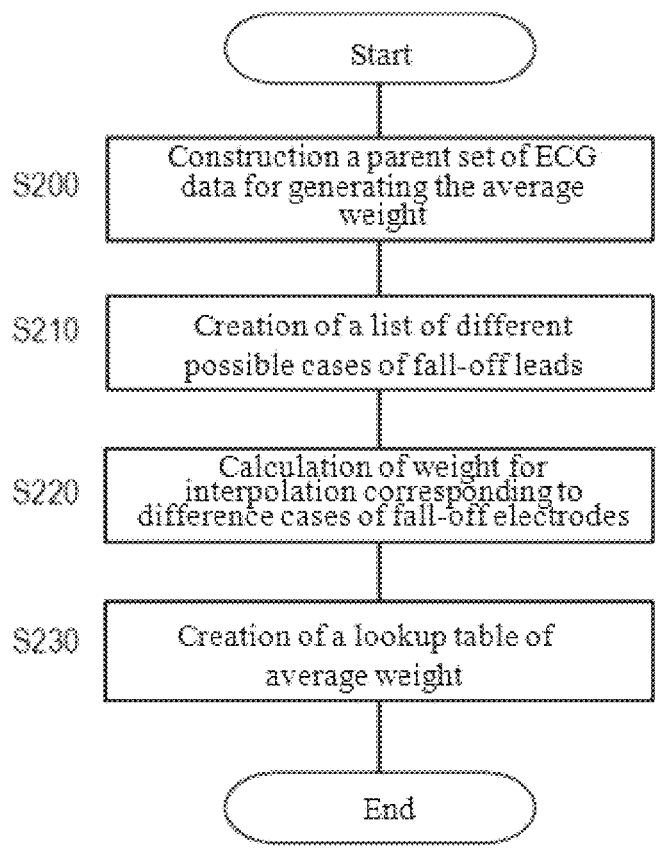
FIG. 13 is a flow chart showing the steps of creating an average weight. (first embodiment).

FIG. 13 is a flowchart showing the steps of creating average weight. Firstly, an ECG data of a population is constructed to generate the average weight (S200). Specifically, ECG data are obtained from an unspecified large number of people according to gender and age. Then, a list of different cases of simulated fall-off leads is made (S210). In the case of acquiring a 12-lead ECG, 8 active measurement electrodes 200A-200F, 200H, 200J and 2 passive measurement electrodes 200G, 200I are attached on the body of subject 150. A list of all cases corresponding to the fall-off electrodes, such as one of the six active measurement electrodes of 200A-200F falls off, and any two of them fall off, etc., in this way, is made according to gender and age (refer to FIG. 9).

Then, the weight used to interpolate the simulated fall-off lead is calculated (S220). Specifically, for example, when only the active measurement electrode 200A falls off, the electrocardiographic signal obtained due to the fall-off is different from the actual electrocardiographic signal. Therefore, the interpolated weight is calculated so that the electrocardiographic signal becomes the same as the actual electrocardiographic signal obtained when the active measurement electrode 200A does not fall off. All cases of fall-off of electrodes are calculated for the weight. And finally a look-up table of the average weight calculated as above is created (S230). The created lookup table is stored in the average weight database 320 (see FIG. 8).

In addition, the average weight will become inaccurate with the passage of time, because with the change of social environment, people's physique and composition of muscle and fat are different for different ages. Therefore, the average weight is preferably to update after each 2 or 3 years.

Figure 14:
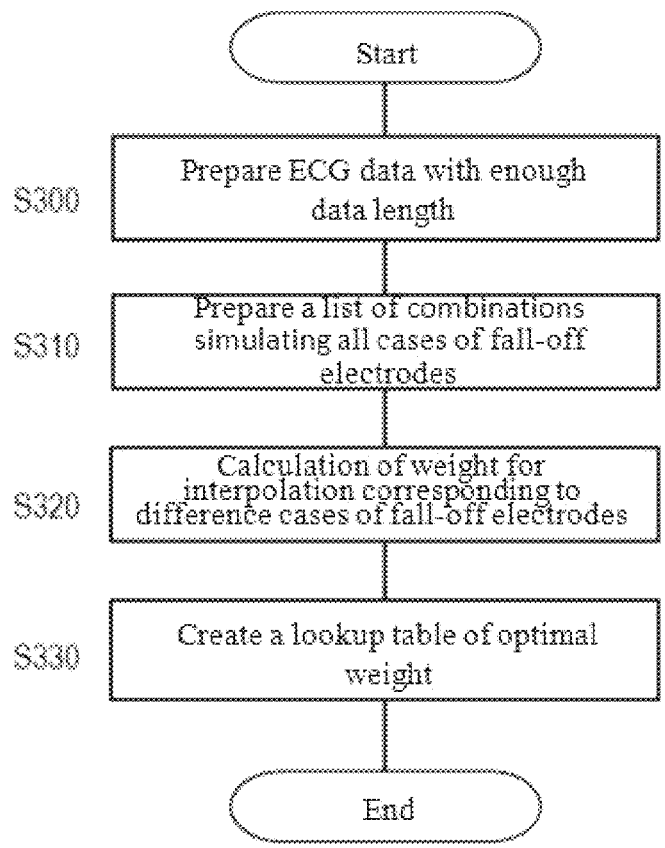
FIG. 14 is a flow chart showing the steps of creating an optimal weight. (first embodiment).

FIG. 14 is a flowchart showing the steps of creating the optimal weight. First of all, prepare the ECG data with enough data length (S300). ECG data from the subject 150 him/herself are preferably to be used as much as possible. Then, a list of combinations simulating different cases of electrode fall-off is made (S310). As mentioned above, in the case of acquiring a 12-lead ECG, eight active measurement electrodes 200A-200F, 200H, 200J and two passive measurement electrodes 200G, 200I are attached on the body of subject 150. A list of all cases of fall-off, such as any one of the six active measurement electrodes 200A-200F falls off, any two of them fall off, etc, is created (refer to FIG. 10).

Then, the weight used to interpolate the simulated fall-off lead is calculated (S320). Specifically, for example, when only the active electrode 200A falls off, the electrocardiographic signal obtained during the fall-off is different from the actual electrocardiographic signal. Therefore, the interpolated weight is calculated so that the electrocardiographic signal becomes the same as the actual electrocardiographic signal obtained when the active measurement electrode 200A does not fall off. All the fall-off cases are calculated for the weight, and finally a look-up table with the optimal weight calculated as above is created (S330). The created lookup table is stored in the optimal weight database 330 (see FIG. 8).

In addition, due to the same reason as the average weight, the optimal weight is preferably to be updated regularly in each 2 or 3 years.

As mentioned above, in the electrocardiograph system 100 of first embodiment, eight active measurement electrodes 200A-200F, 200H and 200J attached on the body of subject 150 have the function of transmitting chest lead signals and limb lead signals. Therefore, when collecting 12-lead ECG, it is not necessary to connect the active measurement electrodes 200A-200F, 200H, 200J to the electrocardiograph body 300 through cables. Therefore, each measurement electrode does not need to be connected with a cable, and the handling of the cable by the measurer becomes easy. And it is possible to achieve an improvement in the handling of the measurement electrodes and cables as desired by medical institutions. Also, it is possible to measure 12-lead ECGs outside medical institutions, especially to carry out 12-lead ECGs in family medical treatment and the like.

In addition, the electrocardiographic signal from the Wilson terminal 180 is input to the active measurement electrodes 200A-200F, and the lead signal of the chest required for the generation of the electrocardiogram is calculated by the active measurement electrodes 200A-200F. Therefore, the lead signal of the chest can be transmitted to the electrocardiograph body 300 through wireless communication.

In the electrocardiograph system 100 of first embodiment, even if when one or more of the six active measurement electrodes 200A-200F attached on the chest of subject 150 falls off, the correct ECG can be acquired without aware of the fall-off. This is because all cases of fall-off of electrode are taken into account when preparing average weight and optimal weight. Thus accurate ECGs can be reliably generated in first embodiment.

[Modification of First Embodiment]

Figure 15:
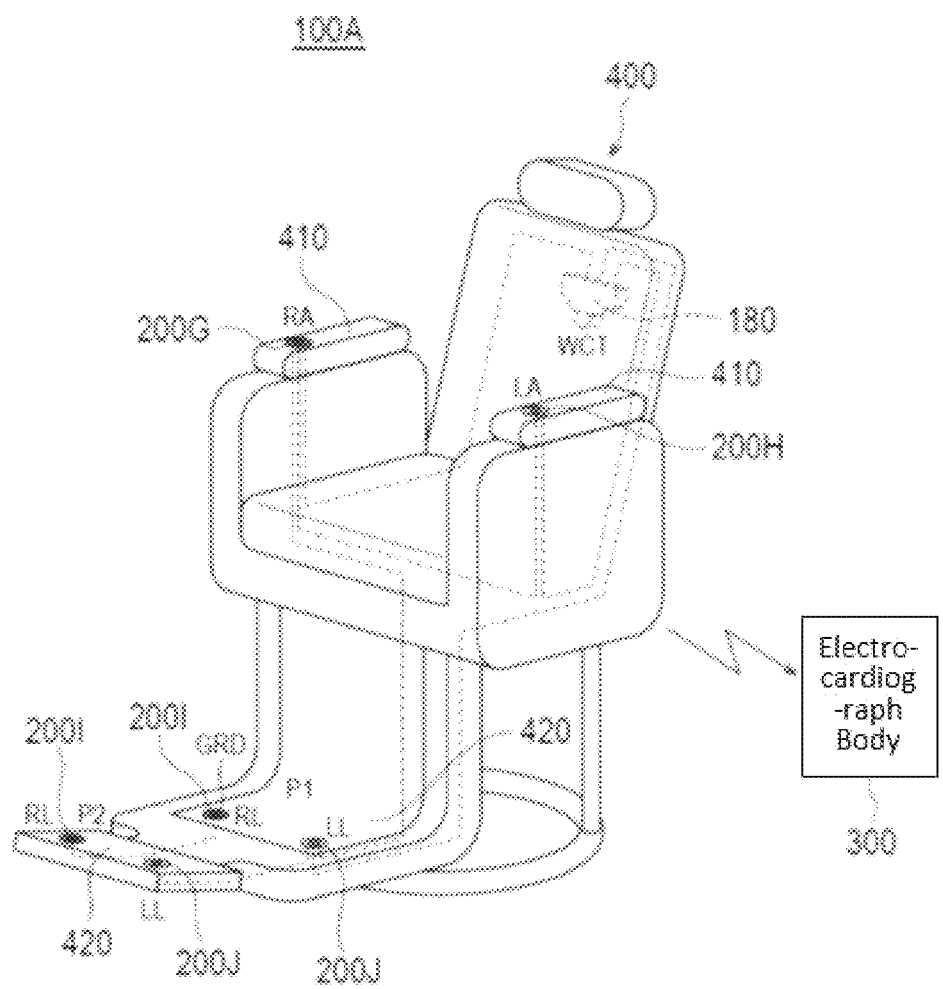
FIG. 15 is a diagram showing a modification of the electrocardiograph system of first embodiment.

FIG. 15 is a diagram showing a modification of the electrocardiograph system 100 of first embodiment. In the modification, passive measurement electrode 200G and active measurement electrode 200H are arranged at armrest 410 on the left and right sides of chair 400, and passive measurement electrode 200I and active measurement electrode 200J are arranged on the left and right sides of footrest 420 with two sections. Therefore, subject 150 does not need to attach the passive measurement electrodes 200G, 200I and active measurement electrodes 200H, 200J measurement electrode on both arms and legs as shown in first embodiment.

The subject 150 sits on the chair 400 with the active measurement electrodes 200A-200F attached, and the electrocardiogram can be collected by contacting the palms of both hands with the passive measurement electrodes 200G and the active measurement electrodes 200H of the left and right armrests 410, and contacting both feet with the passive measurement electrode 200I and the active measurement electrode 200J mounted on either of two sections of the footrests 420. In this way, as long as the subject 150 puts the active measurement electrode 200A-200F on his chest as shown in FIG. 1, and sits on the chair 400, he can collect the electrocardiogram of himself.

The chair 400 shown in FIG. 15 is reclinable. The footrests 420 is divided into two sections so that the position of the foot of the subject 150 can change according to the inclination angle. Passive measurement electrodes 200G, 200I and active measurement electrodes 200H and 200J are configured at the armrests 410 and the footrests 420. Wilson terminal 180 is embedded in chair 400. Wilson terminal 180 is connected to the passive measurement electrode 200G, the active measurement electrode 200H of the armrests 410 and the active measurement electrode 200J of the footrests 420 to form an indifferent electrode. The passive measurement electrode 200I and the active measurement electrode 200J are respectively arranged at each of the footrests 420 of the two sections, and switch to use the passive measurement electrode 200I and the active measurement electrode 200J according to the inclination angle of the subject.

For example, when the subject 150 to whom the active measurement electrodes 200A to 200F are attached takes an electrocardiogram without reclining of the chair 400, his/her feet ride on the passive measurement electrodes 200I and the active measurement electrodes 200J of the footrest 420 on the chair side. On the other hand, in the case of reclining and taking an electrocardiogram in a posture in which the subject 150 lies down, the feet are placed on the passive measurement electrode 200I and the active measurement electrode 200J of the footrest 420 on the distal end side.

In addition, the Wilson terminal 180 built in the chair 400 and the Wilson terminal 180 (refer to FIG. 1) placed on the subject 150 is connected by a signal line not shown.

In the modification of the above first embodiment, except that the passive measurement electrodes 200G, 200I, and the active measurement electrodes 200H and 200J are arranged on the chair 400, other aspects including the actions of the electrocardiograph body 300 are the same as those of the first embodiment. In the modification of first embodiment, because the arms and legs of the subject 150 are not restrained, the subject 150 can take the ECG in a more relaxed state.

In the above, the structure and action of electrocardiograph system 100 are explained through first embodiment and its modification example. For first embodiment and the modification example, the steps of generating ECG are as follows.

[Electrocardiographic Measurement Method]

According to the electrocardiograph system 100 of first embodiment and its modification, the steps until generating the ECG of the subject 150 are as follows.

The electrocardiographic measurement method includes: a stage of acquiring electrocardiographic signals of chest and limbs of subject 150, a stage of generating potential of the indifferent electrode from electrocardiographic signals of right arm, left arm and left leg of subject 150, a stage of transmitting chest lead signals calculated from the potentials of the electrocardiographic signal from the chest and the potential of the indifferent electrode through wireless communication, a stage of transmitting limb lead signals obtained from the potential of the limb electrocardiographic signals through wireless communication, and a stage of generating an ECG based on the transmitted chest lead signals and limb lead signals.

The stage of generating an electrocardiogram further includes: a preparation stage, in order to generate the ECG for the subject 150, making average weight obtained from a non-specific number of population, and making optimal weight obtained from the subject 150, considering any measurement electrodes may fall off; and a stage of generating the ECG of the subject 150 using the optimal weight if the optimal weight of the subject exists in optimal weight database, and otherwise using the average weight if the optimal weight of the subject does not exist.

Second Embodiment (Overall Configuration of Electrocardiograph System)

Figure 16:
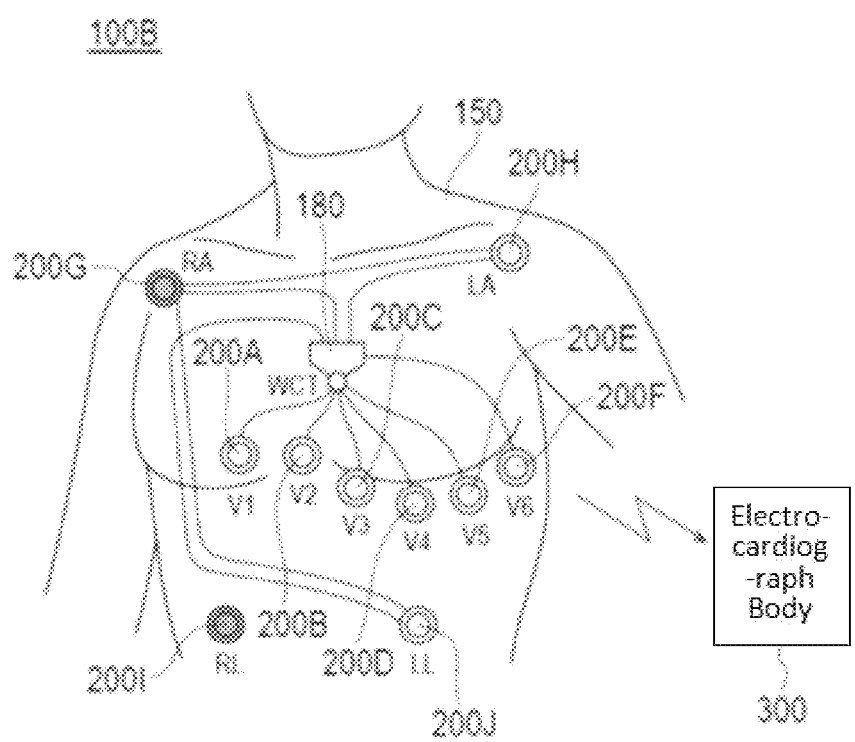
FIG. 16 a structure diagram shows the structure of an electrocardiograph system. (second embodiment).

FIG. 16 is a structure diagram of the electrocardiograph system of the second embodiment. The difference between second embodiment and first embodiment is that the passive measurement electrodes 200G and 200I and the active measurement electrodes 200H and 200J are placed on the trunk of the subject 150. As the same as in first embodiment, take the acquisition of the 12-lead ECG as an example to illustrate.

As shown in FIG. 16, in the case where a 12-lead ECG is acquired in the electrocardiograph system 100B of second embodiment, passive measurement electrode 200G, 200I, active measurement electrode 200H, 200J for acquiring the electrocardiographic signals of the limbs of the subject 150, are placed at four places of the right supraclavicle, the left subclavicle, the right anterior iliac spine or right lower rib arch, and the left anterior iliac spine or left lower rib arch of the trunk of the subject 150. The active measurement electrodes 200A, 200B, 200C, 200D, 200E and 200F for acquiring electrocardiographic signals of the chest of the subject 150 are placed at the specified 6 points of chest of subject 150. In addition, Wilson terminal 180 is provided to form an indifferent electrode by connecting to passive measurement electrode 200G, active measurement electrode 200H and 200J arranged on the right supraclavicle, the left subclavicle, the left anterior iliac spine or left lower rib arch.

The active measurement electrodes 200A, 200B, 200C, 200D, 200E and 200F send the chest lead signals through wireless communication. The chest lead signals are calculated from the potential of electrocardiographic signals acquired by active measurement electrodes 200A, 200B, 200C, 200D, 200E and 200F and the potential of the indifferent electrode of Wilson terminal 180. The active measurement electrode 200H and 200J send the limb lead signals through wireless communication. The limb lead signals is calculated from the potential of electrocardiographic signals of limb obtained from passive measurement electrodes 200G, 200I and active measurement electrode 200H and 200J. Electrocardiograph body 300 generates an ECG based on chest lead signals sent by active measurement electrodes 200A, 200B, 200C, 200D, 200E and 200F and limb lead signals sent by active measurement electrodes 200H and 200J.

(Configuration of Measurement Electrode)

Figure 17A:
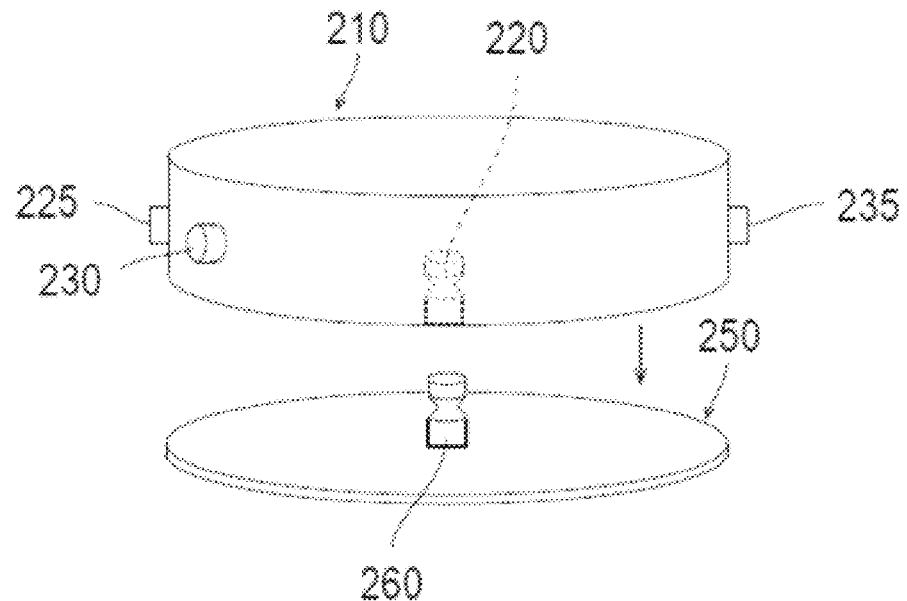
FIG. 17a shows an external view of an active measurement electrode (second embodiment).
Figure 17B:
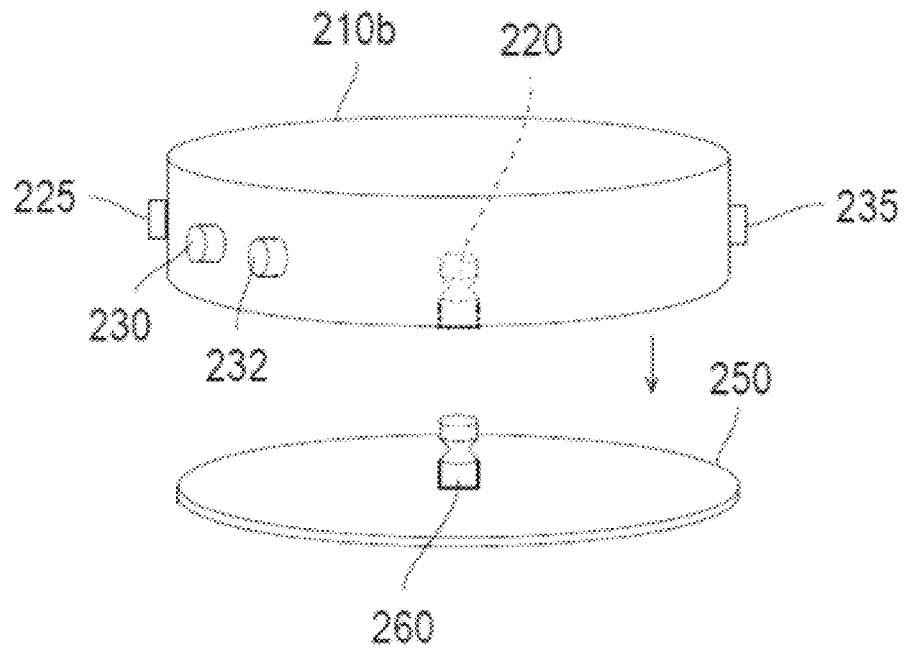
FIG. 17b shows an external view of a passive measurement electrode (second embodiment).

FIG. 17a shows an external view of active measurement electrodes 200A, 200B, 200C, 200D, 200E, 200F, 200H and 200J. In addition, FIG. 17b shows an external view of passive measurement electrodes 200G and 200I. The configuration of these measurement electrodes is the same as those in FIG. 2A and FIG. 2B In addition, the configurations of the control-communication devices 210 and 210b, the patch electrode 250 shown in FIGS. 17A and 17B are the same as those of the control-communication devices 210 and 210a of the first embodiment shown in FIGS. 2A, 2B and FIG. 4, the patch electrode 250 shown in FIGS. 3A and 3B. Further, the configuration of the ECG generator included in the control-communication device 210 of the active measurement electrodes 200A, 200B, 200C, 200D, 200E, 200F, 200H, and 200J is the same as that of the ECG generator 240 of the first embodiment shown in FIG. 5.

In the electrocardiograph system 100b of second embodiment, the action of the measurement electrode is the same as that of the measurement electrode of the electrocardiograph system 100 described in FIG. 6. In addition, the configuration and action of the electrocardiograph body are the same as those of the electrocardiograph body 300 described in FIG. 7-14.

As mentioned above, in the electrocardiograph system 100b of second embodiment, the control-communication device 210 of 8 active measurement electrodes 200A-200F, 200H, 200J, placed on the torso of subject 150 has the function of wirelessly transmitting chest lead signals and limb lead signals. Therefore, similar to the electrocardiograph system 100 of first embodiment, there is no need to wired the active measurement electrode 200A-200F, 200H, 200J and the passive measurement electrodes 200G, 200I to electrocardiograph body 300. Therefore, it is not necessary to connect wires (usually long, thick and heavy) onto each measurement electrode, so that the measurer can use the electrodes more easily.

In addition, the signal from Wilson terminal 180 is directly input to the active measurement electrode 200A-200F, and the chest lead signals required for ECG generation is calculated by operation inside the active measurement electrodes 200A-200F. Thus, the chest lead signals can be transmitted to the electrocardiograph body 300 through wireless communication.

In addition, in the electrocardiograph system 100b of second embodiment, as in the electrocardiograph system 100 of first embodiment, even if there is electrodes fall-off among the six active measurement electrodes 200A-200F placed on the torso of subject 150, a correct ECG can be acquired without being aware of the fall-off. This is because all cases of fall-off of electrode are taken in account when preparing average weight and optimal weight. In second embodiment, because the fall-off lead weight is used, a very reliable ECG can be generated.

Furthermore, in the electrocardiograph system 100b of second embodiment, the passive measurement electrodes 200G and 200I are placed on the trunk of the subject 150. Thus, there is no need for a bed for the subject 150 to lie on. In addition, the subject 150 does not need to lie on the bed 170 when collecting the electrocardiogram as in the first embodiment.

The electrode positions shown in FIG. 16 are also used in the traditional exercise electrocardiograph systems. However, in the past, the electrodes and the host need to be connected by cable, which is a burden for taking ECG while exercising. According to second embodiment, the use of cable is no longer necessary, which makes the exercise electrocardiograph system simpler to acquire an ECG. This is considered a kind of technical innovation.

[Modification of Second Embodiment]

Figure 18:
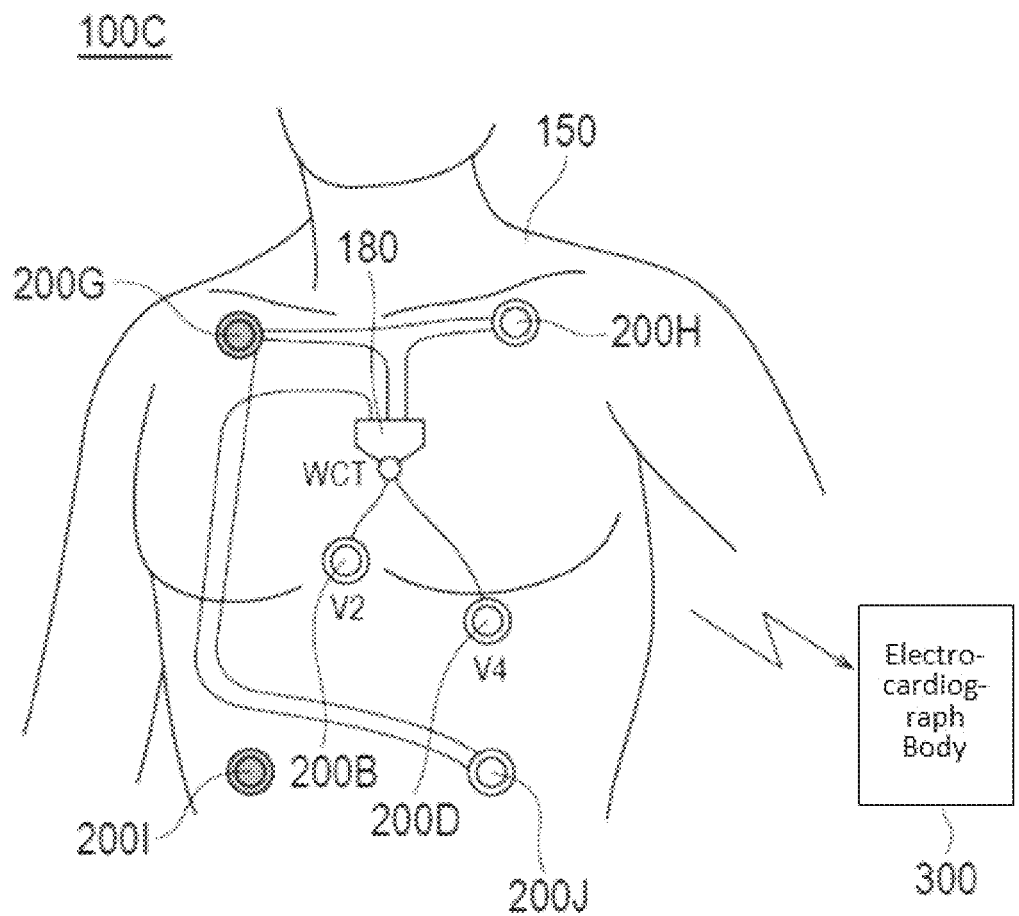
FIG. 18 is a diagram showing a modification of the electrocardiograph system of the second embodiment.

FIG. 18 is a diagram of a modification of the electrocardiograph system 100B of second embodiment. In this case, a configuration for acquire a 4-lead ECG is shown.

As shown in FIG. 18, in the electrocardiograph system 100C according to the variant example of the second embodiment, as a 4-lead electrocardiogram is taken, passive measurement electrodes 200G, 200I and active measurement electrodes 200H and 200J are attached for acquiring electrocardiographic signals of the limbs of the subject 150 at four points of the right supraclavicle, the left subclavicle, the right anterior iliac spine or right lower rib arch, and the left anterior iliac spine or left lower rib arch, on the trunk of the subject 150. Then, at two specified positions on the chest, the active measurement electrodes 200B and 200D for acquiring the electrocardiographic signals of the chest of the subject 150 are placed. In addition, a Wilson terminal 180 to form an indifferent electrode is provided by connecting to the passive measurement electrodes 200G, 200I and active measurement electrodes 200J attached to the right supraclavicle, the left subclavicle, and the left anterior iliac spine or left lower rib arch of the subject 150.

The active measurement electrodes 200B and 200D wirelessly transmit chest lead signals obtained from the potentials of the electrocardiographic signals acquired by the active measurement electrodes 200B and 200D and the potential of the indifferent electrode of the Wilson terminal 180. The active measurement electrodes 200H and 200J transmit the limb lead signals obtained from the potentials of limbs electrocardiographic signals obtained by the passive measurement electrodes 200G and 200I, the active measurement electrodes 200H and 200J through wireless communication. Electrocardiograph body 300 generates ECGs based on chest lead signals transmitted by active measurement electrodes 200B and 200D and limb lead signals transmitted by active measurement electrodes 200H and 200J.

(Action of Measurement Electrode)

Figure 19:
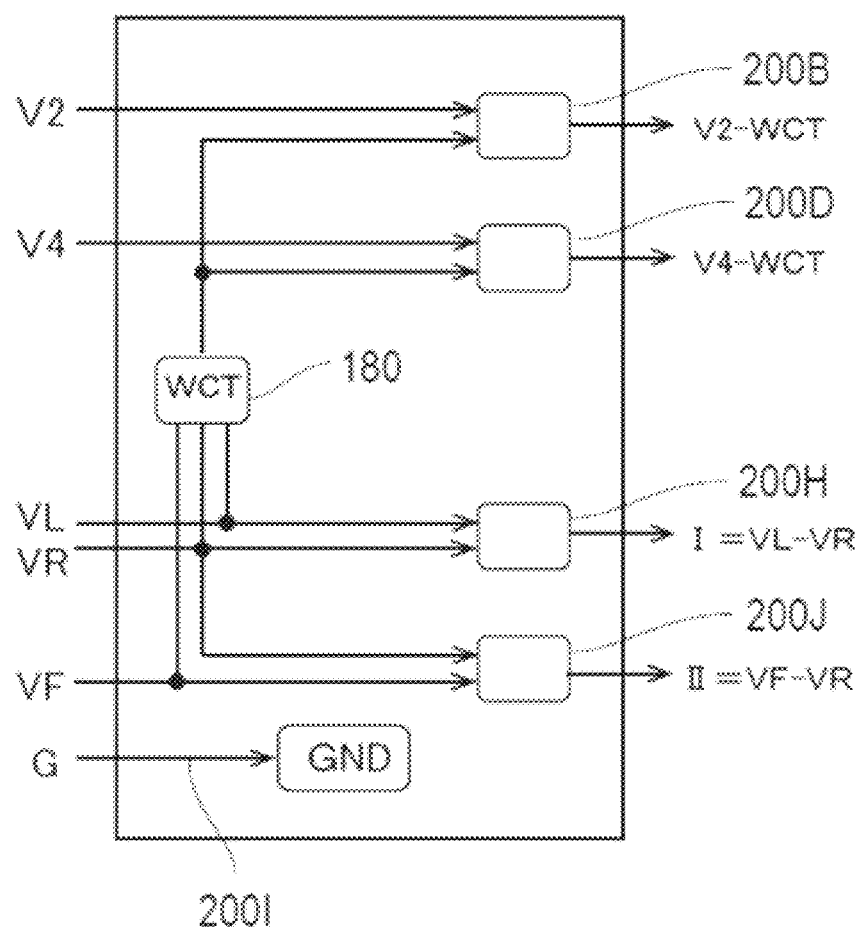
FIG. 19 is a connection diagram of the measurement electrodes of the electrocardiograph system of FIG. 18.

FIG. 19 is a connection diagram of the measurement electrodes of the electrocardiograph system 100C of FIG. 18. The active measurement electrodes 200B and 200D act as follows.

The active measurement electrode 200B inputs the potential V2 of the electrocardiographic signal from the patch electrode 250 of the active measurement electrode 200B through the connector 260, and inputs, through the input terminal 225 of the active measurement electrode 200B, the potential WCT of the electrocardiographic signal output from the Wilson terminal 180. Here, the output potential of electrocardiographic signals of Wilson terminal 180 is the sum of the potential VR of the electrocardiographic signal obtained by the passive measurement electrode 200G on the right supraclavicle, the potential VL of the electrocardiographic signal obtained by the active measurement electrode 200H under the left subclavicle, and the potential VF of the electrocardiographic signal obtained by the active measurement electrode 200J at the left anterior iliac spine or left lower rib arch divided by 3, that is the value of (VR+VL+VF)/3. The active measurement electrode 200B calculates V2-WCT and transmit the result wirelessly as a chest lead signal.

Similarly, the active measurement electrode 200D calculates the V4-WCT and transmits the result wirelessly as a chest lead signal.

The action of passive measurement electrode 200G, 200I, active measurement electrode 200H, 200J is as follows. The passive measurement electrode 200G inputs the potential VR of the electrocardiographic signal from its patch electrode 250 (refer to FIG. 17b) via the connector 260. The potential VR of the electrocardiographic signal is output from the output terminal 230 of passive measurement electrode 200G to active measurement electrode 200H and 200J, and the potential VR of the electrocardiographic signal is also output from output terminal 232 to Wilson terminal 180.

The active measurement electrode 200H inputs the potential VL of the electrocardiographic signal from the patch electrode 250 (refer to FIG. 17a) of the active measurement electrode 200H via the connector 260. The potential VR of the electrocardiographic signal output by the passive measurement electrode 200G is input from the input terminal 225 of the active measurement electrode 200H. VL−VR is calculated by active measurement electrode 200H, and the result is transmitted out wirelessly as limb lead signal. In addition, the potential VL of the electrocardiographic signal is output from the output terminal 232 to the Wilson terminal 180.

The passive measurement electrode 200I inputs the potential G of the electrocardiographic signal from the patch electrode 250 of the passive measurement electrode 200I through the connector 260. The potential G serves as a reference potential (ground) for active measurement electrode 200B, 200D, passive measurement electrode 200G and active measurement electrode 200H, 200J. Thus, the output terminal 230 and 232 of the passive measurement electrode 200I are connected with the grounding terminal 235 of the active measurement electrode 200B, 200D, the passive measurement electrode 200G, and the active measurement electrode 200H, 200J.

The active measurement electrode 200J inputs the potential VF of the electrocardiographic signal from the patch electrode 250 of the active measurement electrode 200J via the connector 260. The input terminal 225 of the active measurement electrode 200J inputs the potential VR of the electrocardiographic signal output by the passive measurement electrode 200G. VF−VR is calculated by active measurement electrode 200J, and the result is transmitted as a limb lead signal wirelessly. In addition, a potential VF of the electrocardiographic signal is output from the output terminal 232 to the Wilson terminal 180.

The structure of the active measurement electrode 200B, 200D, passive measurement electrode 200G, 200I, active measurement electrode 200J, and control-communication device 210 and patch electrode 250 of the active measurement electrode 200B, 200D, 200H and 200J in the modification of second embodiment are the same as those of the electrocardiograph system 100B of the second embodiment. In addition, the structure of the electrocardiograph body 300 and the actions of the electrocardiograph body 300 are the same as those of the electrocardiograph system 100B involved in the second embodiment.

As mentioned above, in the electrocardiograph system 100C of the modification example of second embodiment, the control-communication device 210 of two active measurement electrodes 200B, 200D and two active measurement electrodes 200H, 200J attached on the body of subject 150 has the function of transmitting chest lead signals and limb lead signals. Like the electrocardiograph system 100 of first embodiment, there is no need to connect the active measurement electrodes 200B, 200D, 200H, 200J to the electrocardiograph body 300 by cable.

In addition, in the case of acquiring a 4-lead ECG, there are only two active measurement electrodes 200B and 200D on the chest, so ECG can be taken more easily. Of course, instead of V2 and V4, other leads like V1, V3 can also be used in application.

In addition, in the electrocardiograph system 100C involved in modification of second embodiment, as in the electrocardiograph system 100 involved in first embodiment, even if when one of the two active measurement electrodes 200B and 200D placed on the subject 150 falls off, the correct ECG can be acquired without aware of the fall-off.

[Another Modification of Second Embodiment]

Figure 20:
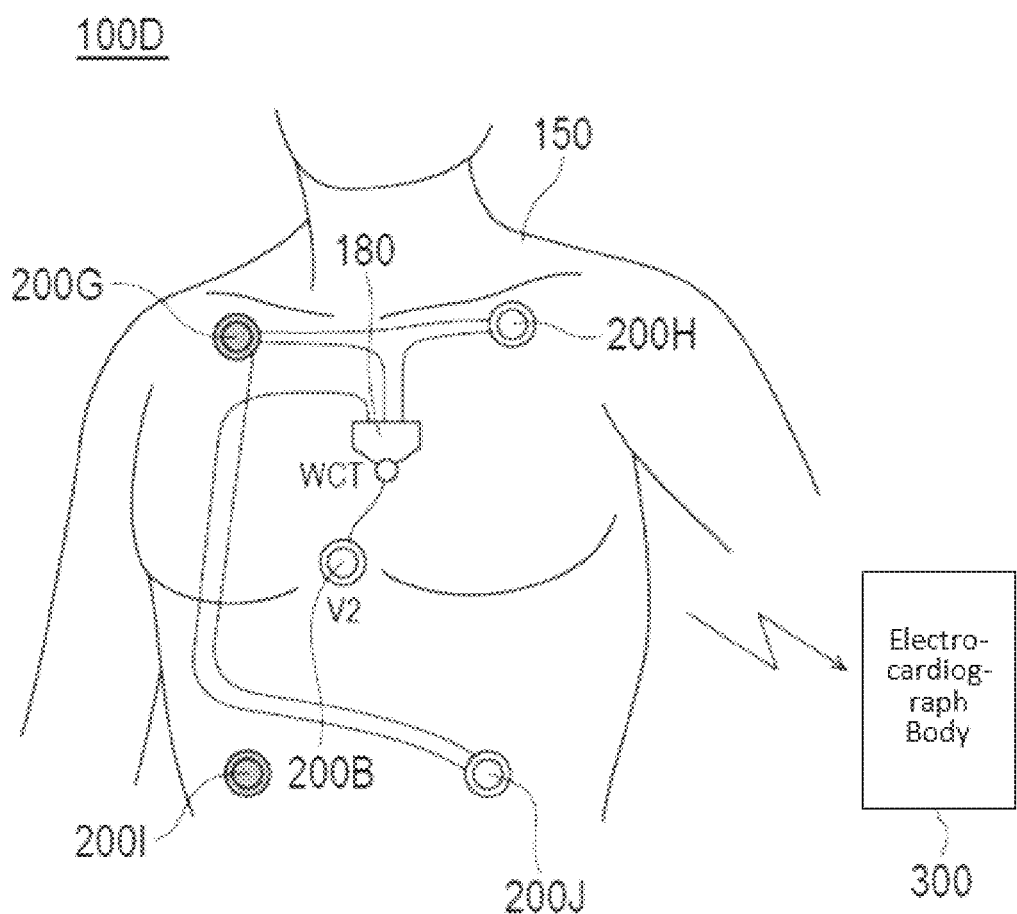
FIG. 20 is a diagram showing another modification of the electrocardiograph system of second embodiment.

FIG. 20 is a diagram showing another modification of the electrocardiograph system 100B of the second embodiment. In this modification, the structure for taking a 3-lead ECG is shown.

As shown in FIG. 20, in the electrocardiograph system 100D of another modification of second embodiment, if a 3-lead ECG is taken, the passive measurement electrodes 200G, 200I and active measurement electrodes 200H and 200J for acquiring electrocardiographic signals of limbs of subject 150 are placed on the trunk of the subject 150 at four locations, including the right supraclavicle, the left subclavicle, the right anterior iliac spine or right lower rib arch, and the left anterior iliac spine or left lower rib arch.

Then, at a specified position of the chest, an active measurement electrode 200B for acquiring the electrocardiographic signal of the chest of the subject 150 is placed. The Wilson terminal 180 is provided to form an indifferent electrode by connecting the passive measurement electrode 200G and the active measurement electrode 200H and 200J attached on the right supraclavicle, the left subclavicle, the left anterior iliac spine or left lower rib arch.

The active measurement electrode 200B transmits the chest lead signal obtained from the potential of the electrocardiographic signal acquired by the active measurement electrode 200B and the potential of the indifferent electrode of Wilson terminal 180 through wireless communication. The active measurement electrodes 200H and 200J transmit the limb lead signals obtained from the potentials of the limbs electrocardiographic signals acquired from the passive measurement electrodes 200G and 200I and the active measurement electrodes 200H and 200J through wireless communication. Electrocardiograph body 300 generates ECG according to the chest lead signal transmitted by active measurement electrode 200B and limb lead signals transmitted by active measurement electrodes 200H and 200J.

[Action of Measurement Electrode]

Figure 21:
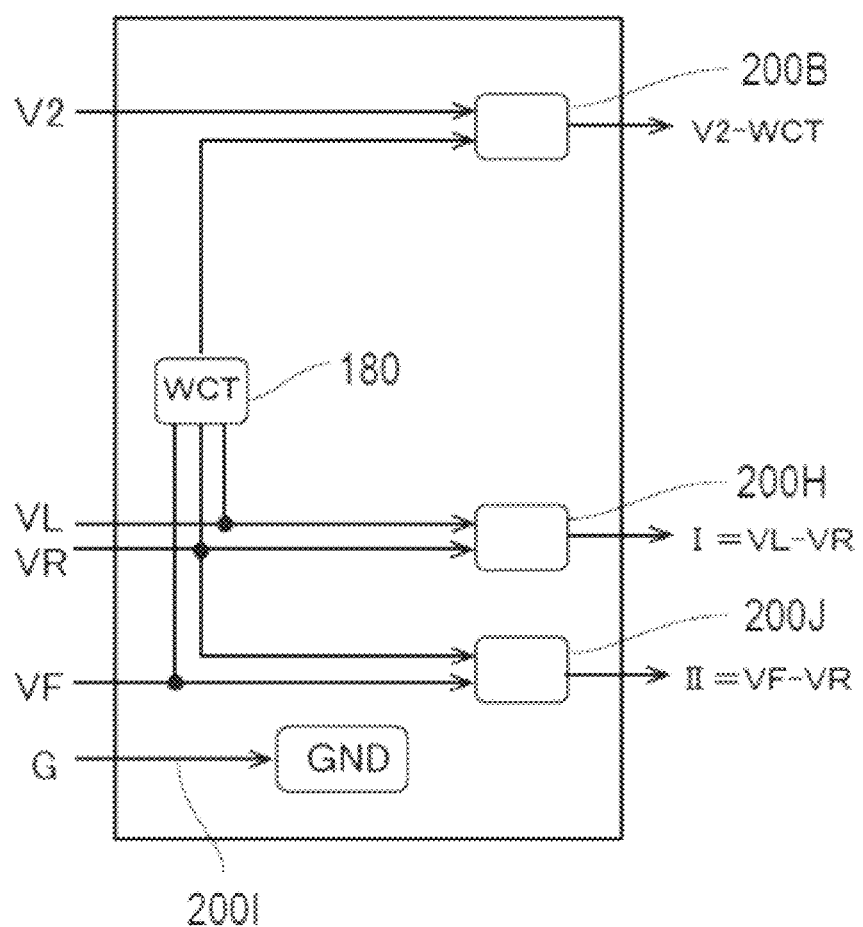
FIG. 21 is a connection diagram of the measurement electrodes of the electrocardiograph system of FIG. 20.

FIG. 21 is a connection diagram of measurement electrode constituting the electrocardiograph system 100D shown in FIG. 20. Firstly, the active measurement electrode 200B acts as follows.

The active measurement electrode 200B inputs the potential V2 of the electrocardiographic signal from the patch electrode 250 of the active measurement electrode 200B through the connector 260, and input the potential WCT of the electrocardiographic signal from the output of the Wilson terminal 180 through the input terminal 225 of the active measurement electrode 200B. Here, the potential of the electrocardiographic signal output by Wilson terminal 180 is the sum of The potential VR of the electrocardiographic signal acquired by the passive measurement electrode 200G on the right supraclavicle, the potential VL of the electrocardiographic signal acquired by the active measurement electrode 200H under the left subclavicle, and the potential VF of the electrocardiographic signal acquired by active measurement electrode 200J at the left anterior iliac spine or left lower rib arch, divided by 3, namely (VR+VL+VF)/3. The active measurement electrode 200B calculates V2-WCT and transmits the result wirelessly as chest lead signal.

Then, The actions of passive measurement electrodes 200G, 200I, and active measurement electrodes 200H, 200J are as follows. The passive measurement electrode 200G inputs the potential VR of the electrocardiographic signal from the patch electrode 250 (refer to FIG. 17B) of the passive measurement electrode 200G via the connector 260. The output terminal 230 of passive measurement electrode 200G outputs the potential VR of the electrocardiographic signal to active measurement electrode 200H and 200J. Meantime, the potential VR of electrocardiographic signal is output from the output terminal 232 to the Wilson terminal 180.

The active measurement electrode 200H inputs the potential VL of the electrocardiographic signal from the patch electrode 250 (refer to FIG. 17A) of the active measurement electrode 200H via the connector 260. The potential VR of the electrocardiographic signal output by the passive measurement electrode 200G is input from the input terminal 225 of the active measurement electrode 200H. VL–VR is then calculated by active measurement electrode 200H, and the results is transmitted as limb lead I, wirelessly. Meantime, the potential VL of the electrocardiographic signal is output from the output terminal 232 to the Wilson terminal 180.

In addition, the passive measurement electrode 200I inputs a potential G of the electrocardiographic signal from the patch electrode 250 of the passive measurement electrode 200I through the connector 260. The potential G serves as a reference potential (ground) for the active measurement electrode 200B, passive measurement electrode 200G and active measurement electrode 200H, and 200J. Thus, the output terminal 230 and 232 of the passive measurement electrode 200I are connected with the grounding terminal 235 of the active measurement electrode 200B, 200H, 200J and the passive measurement electrode 200G.

The active measurement electrode 200J inputs the potential VF of the electrocardiographic signal from the patch electrode 250 of the 200J via the connector 260. The potential VR of the electrical signal output by the passive measurement electrode 200G is input from the input terminal 225 of the 200J. VF–VR is calculated by active measurement electrode 200J, and the results are transmitted as limb lead signals wirelessly. Meantime, the potential VF is output from output terminal 232 to Wilson terminal 180.

The structure of active measurement electrodes 200B, 200H, 200J, passive measurement electrodes 200G, 200I, as well as the structure of the control-communication device 210 and patch electrode 250 of active measurement electrodes 200B, 200H and 200J in electrocardiograph system 100D involved in another modification of second embodiment, are the same as those of electrocardiograph system 100B of second embodiment. In addition, the structure of the electrocardiograph body 300 and the actions of the electrocardiograph body 300 are the same as those of the electrocardiograph system 100B involved in the second embodiment.

As mentioned above, in the electrocardiograph system 100D according to another modification of Second embodiment, the control-communication device 210 of the three active measurement electrodes 200B and 200H and 200J placed on the subject 150, has a function of transmitting lead signals of the chest and the limbs. Therefore, like the electrocardiograph system 100 of first embodiment, there is no need to wire the active measurement electrodes 200B and 200H and 200J, passive measurement electrodes 200G and 200I to the electrocardiograph body 300.

In addition, in the case of acquiring a 3-lead ECG, Only one active measurement electrode 200B is sufficient, so it is easier to take ECG. In the above example, lead V2 are used, but of course, V1, V3 and other chest leads can also be used.

In addition, even in the electrocardiograph system 100D related to another modification of second embodiment, like the electrocardiograph system 100 involved in first embodiment, even if when the active measurement electrode 200B placed on the subject 150 falls off, it is also possible to acquire the correct ECG without realizing that it falls off.

In the above, the structure and action of electrocardiograph system 100B, 100C and 100D are explained in second embodiment, as well as its two modifications. In second embodiment and the two modifications, the steps till ECG is generated are as follows.

[Electrocardiographic Measurement Method]

According to the electrocardiograph system 100B, 100C and 100D of second embodiment and its two modifications, the steps till generation of the ECG of subject 150 are as follows.

They are:

a stage of acquiring the electrocardiographic signals of the chest and limbs of the subject 150, a stage of generating the potential of indifferent electrode from the electrocardiographic signals of the right supraclavicle, the left subclavicle, and the left anterior iliac spine or left lower rib arch among the electrocardiographic signals of the limbs of the subject 150, a stage of transmitting chest lead signals obtained from the potential of the electrocardiographic signals of the chest and the potential of indifferent electrodes by wireless communication, a stage of transmitting limb lead signals obtained from the potential of the electrocardiographic signals of the limb by wireless communication, and a stage of generating an electrocardiogram based on the transmitted chest lead signals and the transmitted limb lead signals.

In the stage of generating an ECG includes:

a stage of preparing an average weight obtained from an unspecified number of population in order to make an ECG of the subject 150 while taking into account that any one of the measurement electrodes falls off and preparing an optimal weight obtained from the subject 150 in order to make an ECG of the subject 150 while taking into account that any one of the measurement electrodes falls off, and a step of generating the ECG of subject 150 using optimal weight of the subject 150 if there is optimal weight of subject 150, or using the average weight otherwise.

Third Embodiment

[Clothes Making Up the Electrocardiograph System]

Figure 22:
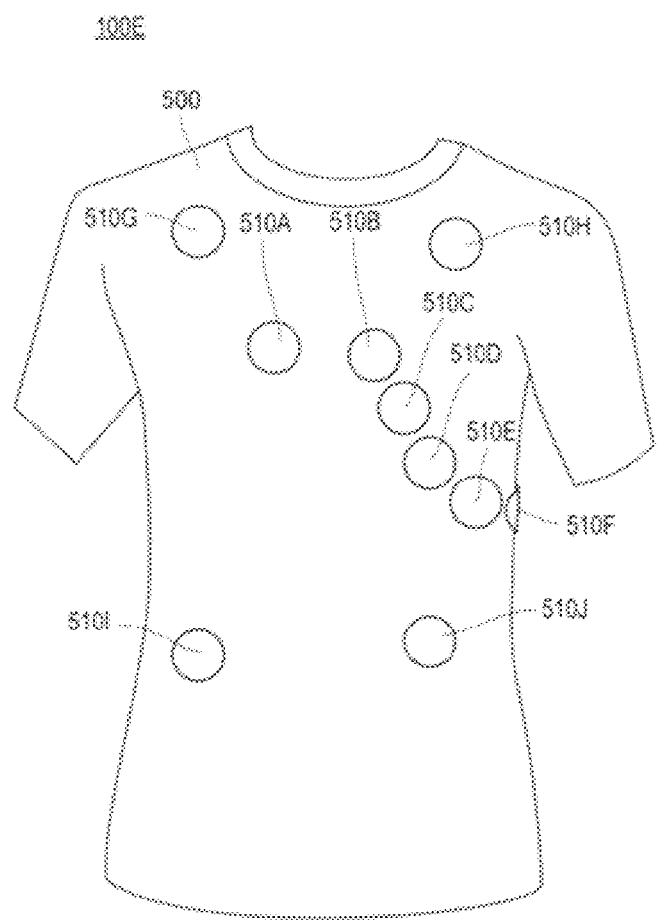
FIG. 22 is a structure diagram of clothes constituting an electrocardiograph system. (third embodiment).
Figure 23:
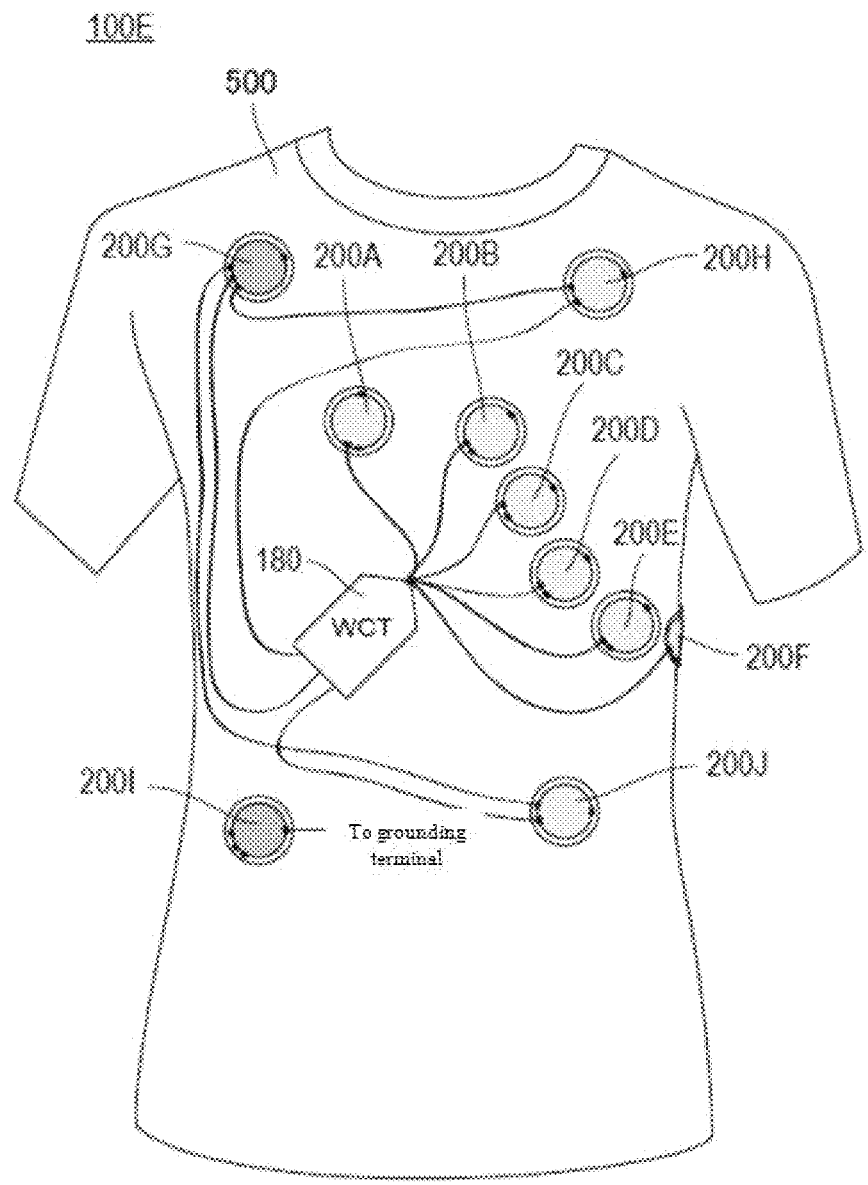
FIG. 23 is a diagram showing a scene where measurement electrodes are placed on the chest and limbs guided by mounting holes of the clothes. (third embodiment).

FIG. 22 is a structure diagram of the clothes of the electrocardiograph system 100E in the third embodiment, and FIG. 23 is a schematic diagram of placing the measurement electrodes of the chest and limbs according to the holes of the clothes.

In third embodiment, a T-shirt 500 is used as the clothes. In addition to T-shirts, you can also use y-shirts, polo shirts, etc. As shown in FIG. 22, in the electrocardiograph system 100E of the third embodiment, active measurement electrodes 200A-200F, 200H, 200J, and passive measurement electrodes 200G and 200I can be mounted by the subject 150 him/herself. Therefore, as shown in FIG. 22, it is possible to make openings in a general T-shirt, for example, the openings include mounting holes 510A-510F indicating the mounting positions of the active measurement electrodes 200A-200F, and mounting holes 510G-510J indicating the mounting positions of the passive measurement electrodes 200G and 200I and the active measurement electrodes 200H and 200J (portions surrounded by circles in the figure). The size of holes is suggested the same or slightly larger than the size of the active measurement electrodes 200A-200F, 200H, 200J and the passive measurement electrodes 200G, 200I.

The mounting holes 510A-510J opened on the T-shirt 500 are designed personally for the subject 150 so as to take the best electrocardiographic signals of the subject 150. The best positions of active measurement electrodes 200A-200F, 200H, 200J and passive measurement electrodes 200G, 200I are different according to the subject 150. Therefore, the positions of mounting holes 510A-510J are determined to make the active measurement electrodes 200A-200F, 200H, 200J and passive measurement electrodes 200G and 200I of chest and limbs to be installed in the best position of the subject 150. The mounting holes 510A-510J are used as guide for the subject 150 to install the active measurement electrodes 200A-200F, 200H, 200J and passive measurement electrodes 200G and 200I in the chest and limbs for him/herself.

As shown in FIG. 23, a Wilson terminal 180 is provided on the T-shirt 500. The function of Wilson terminal 180 is as described above.

In third embodiment, the subject 150 is wearing the T-shirt 500, mounts the active measurement electrodes 200A-200F, 200H, 200J and passive measurement electrodes 200G, 200I for chest and limbs according to mounting holes 510A-510J made on the T-shirt 500, and the connect Wilson terminal 180 with respective chest electrodes 200A-200F. And, the Wilson terminal 180 is connected to the active measurement electrodes 200A-200F, 200H, 200J and the passive measurement electrodes 200G, 200I of the chest and limbs, respectively. In this way, the electrocardiograph system 100B of second embodiment shown in FIG. 16 is realized.

In third embodiment, T-shirt 500 is used as a guide for mounting active measurement electrodes 200A-200F, 200H, 200J and passive measurement electrodes 200G, 200I for chest and limbs. Also, the action and the like of the electrocardiograph system is the same as that of the electrocardiograph system 100B (refer to FIG. 14) of second embodiment.

In this way, according to the electrocardiograph system 100E of third embodiment, the subject 150 is wearing the T-shirt 500 which is provided with mounting holes 510A-510J, and all the electrodes of the active measurement electrodes 200A-200F, 200H, 200J and the passive measurement electrodes 200G, 200I corresponding to the chest and the limbs are respectively installed, thereby completing the placing of the active measurement electrodes 200A-200F, 200H, 200J and the passive measurement electrodes 200G, 200I for the chest and the limbs. In addition, in the case of acquiring a 12-lead ECG, medical education training is required to correctly mount electrodes, but if the T-shirt 500 is used, medical education training is not required. This way, as for taking 12-lead ECG, one does not have to go to the hospital but does it at home.

[Modification of Third Embodiment]

(Clothes that Make Up the Electrocardiograph System)

Figure 24:
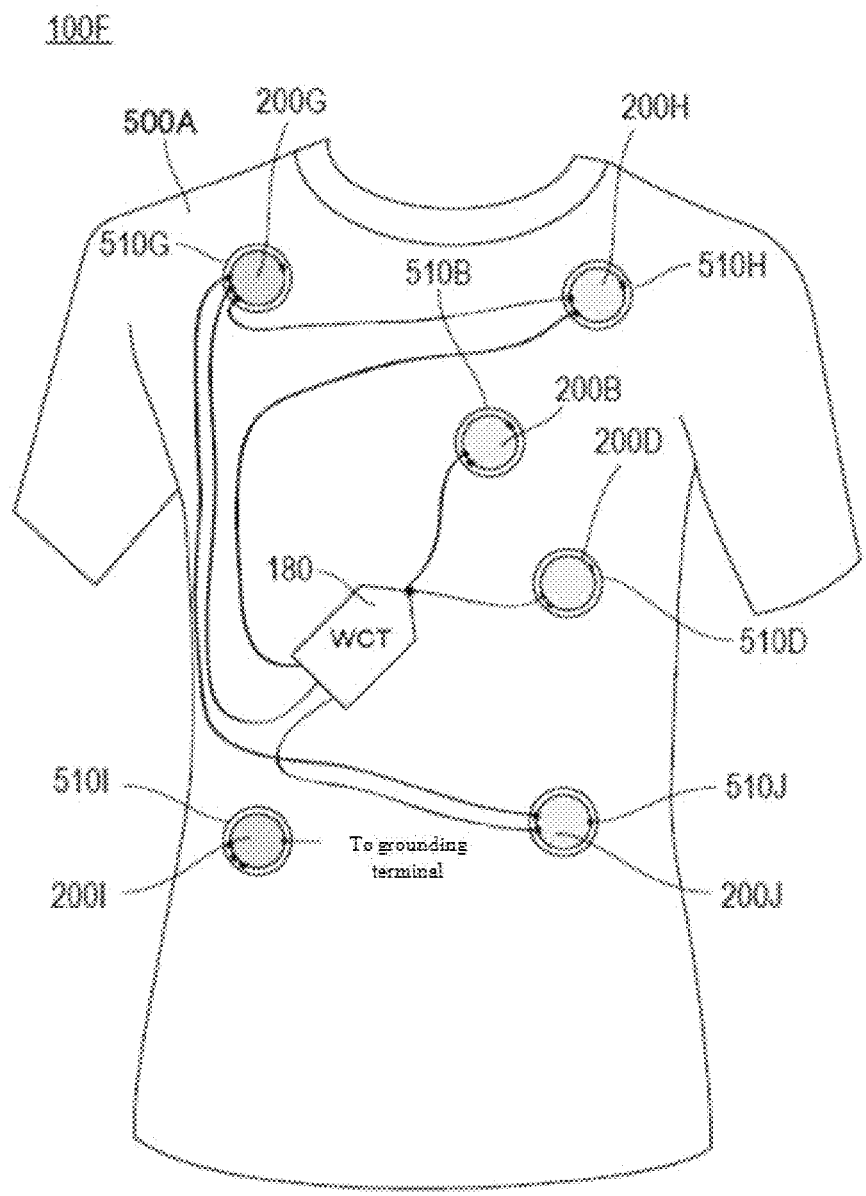
FIG. 24 is a diagram showing a modification of the electrocardiograph system of third embodiment.

FIG. 24 is a diagram showing a modification of the electrocardiograph system 100F of third embodiment. In this modification, the T-shirt 500A is used as a garment. The T-shirt 500A has six mounting holes, 510B, 510D, 510G-510J, where the active measurement electrodes 200B, 200D, 200H, 200J, and the passive measurement electrodes 200G and 200I are mounted, respectively.

In the modification of third embodiment, the subject 150 is wearing a T-shirt 500, and the active measurement electrodes 200B, 200D, 200H, 200J and the passive measurement electrodes 200G and 200I are mounted in the mounting holes 510B, 510D, 510G-510J arranged on the T-shirt 500. Wilson terminal 180 is connected with active measurement electrodes 200B, 200D, 200H, 200J and passive measurement electrodes 200G of the chest and limbs, respectively. In this way, it is possible to realize the electrocardiograph system 100C of the modification of second embodiment shown in FIG. 18.

In the modification of third embodiment, T-shirt 500A is used as the guide for mounting active measurement electrodes 200B, 200D, 200H, 200J and passive measurement electrodes 200G and 200I for chest and limbs. The action of the electrocardiograph system is the same as that of the electrocardiograph system 100C (refer to FIG. 18) in the modification of second embodiment.

In this way, according to the electrocardiograph system 100F of the modification of embodiment 3, the measurement of 4-lead ECG can be carried out simply at home without having to go to the hospital. In the above example, V2 and V4 lead are used, of course, V1, V3 and other chest lead can also be used.

Fourth Embodiment (Configuration of Electrocardiograph System)

Figure 25:
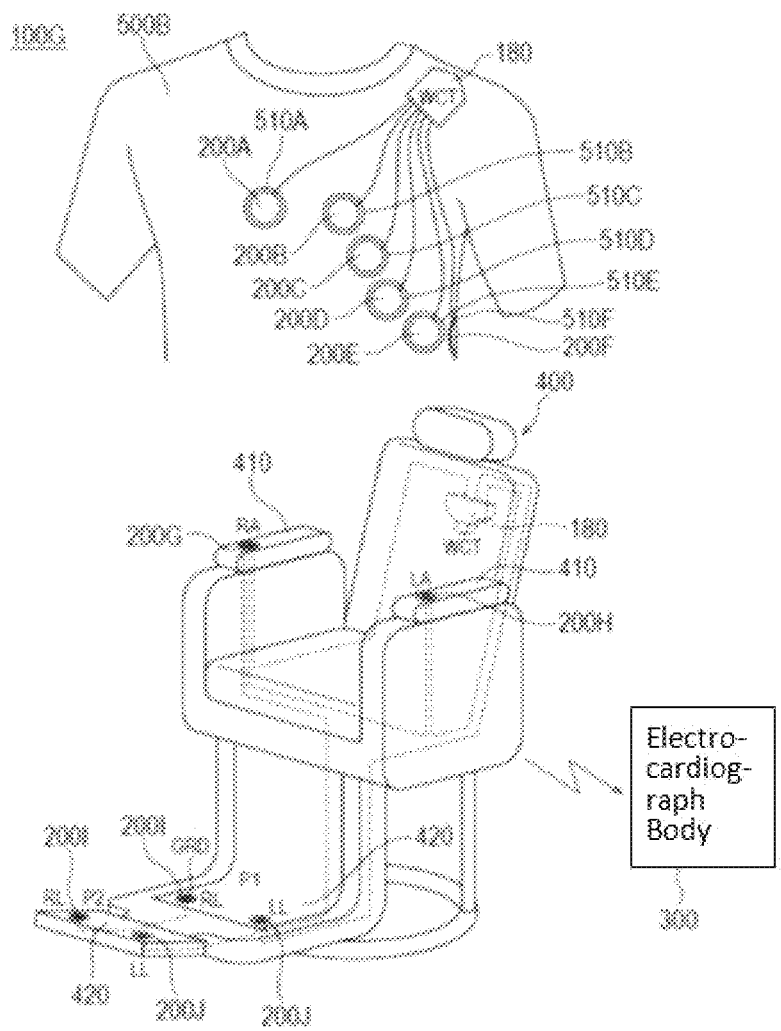
FIG. 25 shows the structure of the electrocardiograph system. (fourth embodiment).

FIG. 25 is a structure diagram of the electrocardiograph system 100G of fourth embodiment. In fourth embodiment, the active measurement electrodes 200A-200F are mounted according to the mounting holes 510A-510F of the T-shirt 500B, the passive measurement electrodes 200G, 200I and active measurement electrodes 200H and 200J are arranged on the chair 400. The electrocardiographic signals obtained from active electrodes 200A-200F, 200H, 200J, and passive electrodes 200G and 200I are transmitted to the electrocardiograph body 300 wirelessly. The electrocardiograph body 300 generates the ECG of subject 150 based on the received electrocardiographic signals.

As shown in FIG. 25, the Wilson terminal 180 is arranged on the T-shirt 500B. And its function is as described above.

In the electrocardiograph system 100G of fourth embodiment, the subject 150 is wearing a T-shirt 500B, and mounts the active measurement electrodes 200A-200F on the mounting holes 510A-510F arranged on the T-shirt 500B. Moreover, the Wilson terminal 180 of T-shirt 500B is connected with respective active measurement electrodes 200A-200F, and the Wilson terminals in the T-shirt 500B and on the chair 400 are connected to each other. The subject 150 is sitting on the chair 400, making the palms and feet contacting the passive measurement electrode 200G, 200I and the active measurement electrode 200H, 200J. In this simple way, it is possible to realize the electrocardiograph system 100A involved in the modification of first embodiment shown in FIG. 15.

In fourth embodiment, the T-shirt 500B is used as a guide for mounting active measurement electrodes 200A-200F. In addition, the actions of the electrocardiograph system are the same as that of the electrocardiograph system 100A (refer to FIG. 15) involved in the modification of first embodiment.

The function provided by the electrocardiograph system 100G of fourth embodiment enables the measurement of 12-lead ECG at home without having to go to the hospital. In addition, because the 12-lead ECG can be measured by only sitting on chair 400, subject 150 can take ECG in a more relaxed state.

[Modification of Fourth Embodiment]

(Configuration of Electrocardiograph System)

Figure 26:
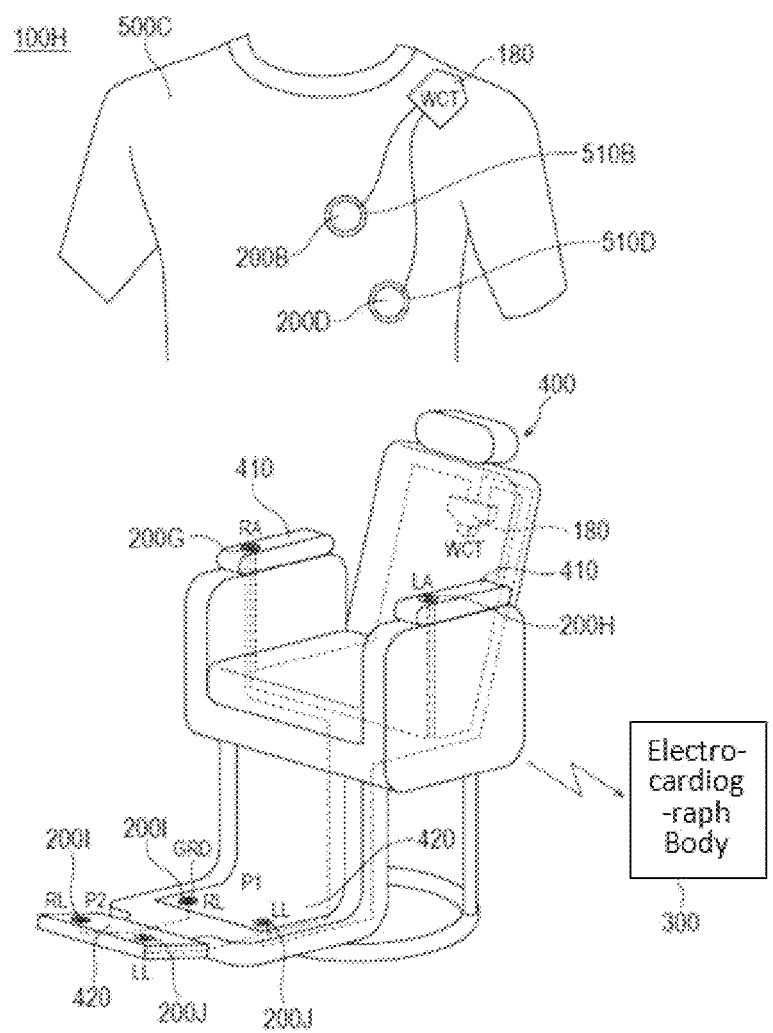
FIG. 26 is a diagram showing a modification of the electrocardiograph system of fourth embodiment.

FIG. 26 is a diagram showing a modification of the electrocardiograph system 100G of the fourth embodiment. In the modification of the fourth embodiment, a 4-lead ECG is acquired. The active measurement electrodes 200B and 200D of electrocardiograph system 100H are mounted with use of mounting holes 510B and 510d of T-shirt 500C. The passive measurement electrodes 200G, 200I and active measurement electrodes 200H and 200J are arranged on the chair 400. The electrocardiographic signals from the active measurement electrodes 200B, 200D, 200H and 200J are transmitted to the electrocardiograph body 300 through wireless communication. The electrocardiograph body 300 generates the ECG of subject 150 using the received electrocardiographic signals.

Even in the case of this embodiment, same as the electrocardiograph system 100G of embodiment 4, the subject 150 is wearing a T-shirt 500C, mounting active measurement electrodes 200B and 200D to the mounting holes 510B and 510D opened in the T-shirt 500C. Moreover, as long as subject 150 sits on the chair 400 and make the palms and feet contact the passive measurement electrodes 200G, 200I and the active measurement electrodes 200H, 200J, 4-lead ECG can be generated.

In this case, the action of the electrocardiograph system is the same as that of the electrocardiograph system 100C of the modification of embodiment 2 (refer to FIG. 18). Therefore, the subject does not have to go to the hospital but can easily test his/her own ECG at home. In this example, although V2 and V4 lead are used, and of course, V1, V3 and other chest lead can also be used instead.

Figure 27:
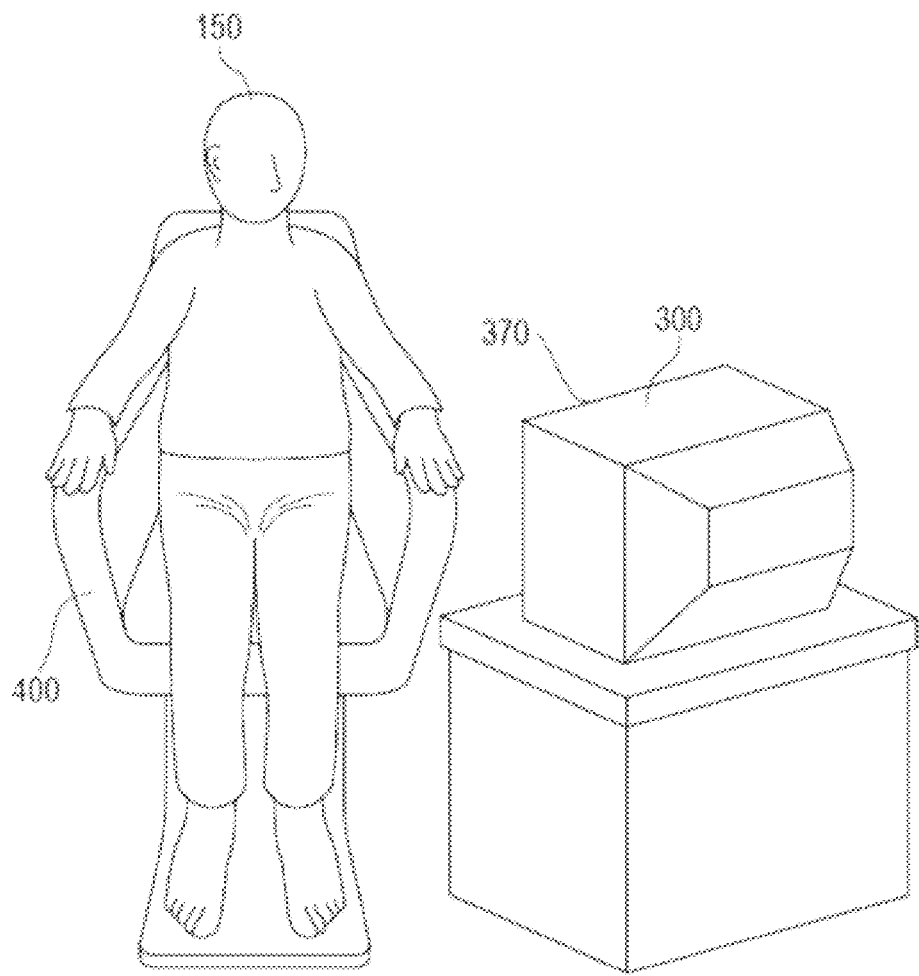
FIG. 27 is a diagram shows a scene of ECG test using the electrocardiograph system of fourth embodiment and a modification thereof.
Figure 28:
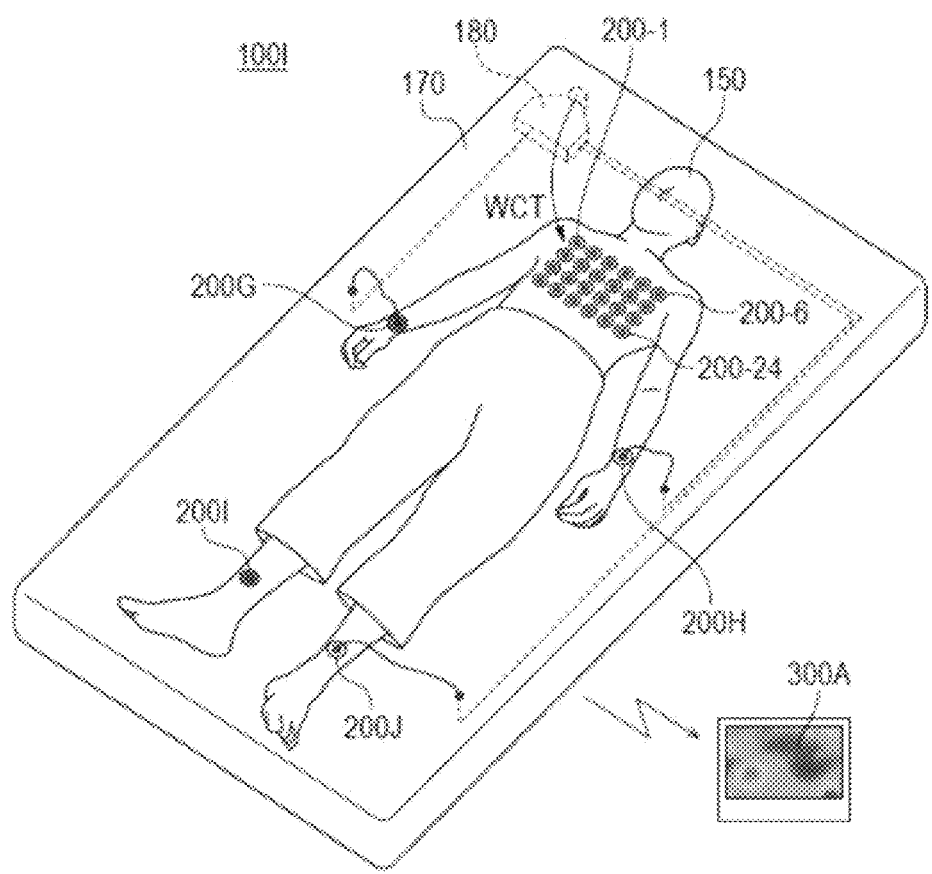
FIG. 28 is a structure diagram of the electrocardiograph system. (fifth embodiment).

FIG. 27 is a scene diagram of electrocardiograph measurement using the electrocardiograph system of fourth embodiment and its modification. FIG. 27 shows a scene that, in the implementation of the fourth embodiment and its modification shown in FIG. 25 and FIG. 26, the subject 150 sits on the chair 400, watches the display 370 of the electrocardiograph body 300 as if watching a TV, and can take the ECG. So that an ECG can also be taken at home in a relaxed state Fifth Embodiment FIG. 28 is a structure diagram of the electrocardiograph system 100I of fifth embodiment. The 100I is an electrocardiograph system taking the body surface mapping ECG.

As shown in FIG. 28, in the electrocardiograph system 100I of fifth embodiment, the subject 150 is lying on the bed 170. Then, the passive measurement electrodes 200G, 200I and active measurement electrodes 200H, 200J are used to acquire the electrocardiographic signals of limbs of the subject 150 by attaching the electrodes at four places of the hands and feet. In addition, the active measurement electrodes 200-1 to 200-24, which can acquire electrocardiographic signals of subject 150, are placed at specified 24 points of the chest and abdomen. The passive measurement electrodes 200G and active measurement electrodes 200H and 200J arranged on the right arm, left arm and left leg of the subject 150 are connected to the Wilson terminal 180 to form indifferent electrodes. The input terminal of the Wilson terminal 180 is connected to the passive measurement electrode 200G and the active measurement electrodes 200H and 200J, and the output terminal of the Wilson terminal 180 is connected to the active measurement electrodes 200-1 to 200-24.

The active measurement electrodes 200H and 200J transmit the lead signals of the limbs which are acquired from the potentials of the electrocardiographic signals of the limbs obtained from the passive measurement electrodes 200G and 200I and the active measurement electrodes 200H and 200J through wireless communication. The active measurement electrodes 200-1 to 200-24 transmit the lead signals of the chest which are acquired from the potentials of the electrocardiographic signals acquired from the active measurement electrodes 200-1 to 200-24 and the potentials of indifferent electrodes of the Wilson terminal 180 through wireless communication. According to the chest lead signals sent by the active measurement electrodes 200-1 to 200-24 and the limb lead signals sent by the active measurement electrodes 200H and 200J, the electrocardiograph body 300A generates the body surface mapping ECG as shown in the figure.

Figure 29:
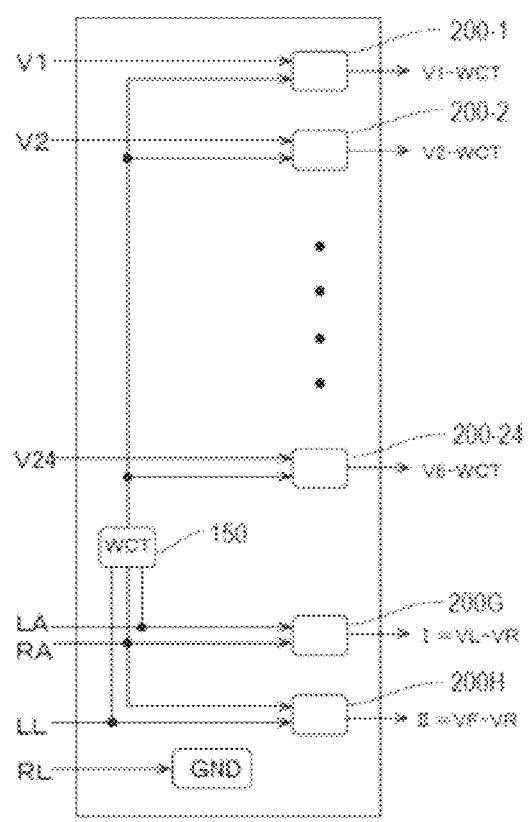
FIG. 29 is a connection diagram of the measurement electrodes of the electrocardiograph system of FIG. 28.

FIG. 29 is a connection diagram of the measurement electrodes that configure the electrocardiograph system of FIG. 28.

The active measurement electrode 200-1 inputs the potential V1 of the electrocardiographic signal from the patch electrode 250 of the active measurement electrode 200-1 via the connector 260. And, the potential WCT of the electrocardiographic signal output from Wilson terminal 180 is input from input terminal 225 of active measurement electrode 200-1. Here, the potential of the electrocardiographic signal output by Wilson terminal 180 is a value obtained by dividing the sum of the potential VR of the electrocardiographic signal acquired by the passive measurement electrode 200G of the right arm, the potential VL of the electrocardiographic signal acquired by the active measurement electrode 200H of the left arm, and the potential VF of the electrocardiographic signal acquired by the active measurement electrode 200J of the left leg by 3, that is, the value of (VR+VL+VF)/3. The active measurement electrode 200-1 calculates V1-WCT and transmits wirelessly the result as chest lead signal.

Similarly, the active measurement electrode 200-2 inputs the potential V2 of the electrocardiographic signal from the patch electrode 250 of the active measurement electrode 200-2 via the connector 260, and input the potential WCT of the electrocardiographic signal output from the Wilson terminal 180 from the input terminal 225 of the active measurement electrode 200-2. The active measurement electrode 200-2 calculates V2-WCT and transmit the result as chest lead signal wirelessly. In the same way, the active measurement electrodes 200-3 to 200-24 calculate chest lead signals and transmit them wirelessly, respectively.

The passive measurement electrodes 200G, 200I, active measurement electrodes 200H, 200J operate as follows. The passive measurement electrode 200G inputs the potential VR of the electrocardiographic signal from the patch electrode 250 of the passive measurement electrode 200G through the connector 260, and outputs the potential VR of the electrocardiographic signal from the output terminal 230 of the passive measurement electrode 200G to the active measurement electrode 200H and the active measurement electrode 200J.

The active measurement electrode 200H inputs the potential VL of the electrocardiographic signal from the patch electrode 250 of the active measurement electrode 200H via the connector 260, and inputs potential VR of the electrocardiographic signal output from the passive measurement electrode 200G from the input terminal 225 of the passive measurement electrode 200G. The active measurement electrode 200H calculates VL–VR and wirelessly transmits the result as a limb lead signal.

Meantime, the active measurement electrode 200H outputs the potentials VL and VR of the electrocardiographic signals from the output terminals 230 and 232 to the Wilson terminal 180.

The passive measurement electrode 200I outputs the potential of the electrocardiographic signal from the patch electrode 250 of the active measurement electrode 200H to the active measurement electrodes 200-1 to 200-24, 200H and 200J of the chest and limbs and the ground terminal 235 of the passive measurement electrode 200G of the chest and limbs via the connector 260. This potential becomes the ground potential (GND).

The active measurement electrode 200J inputs the potential VF of the electrocardiographic signal from the patch electrode 250 of the active measurement electrode 200J via the connector 260, and inputs the potential VR of the electrocardiographic signal output from the passive measurement electrode 200G from the input terminal 255 of the active measurement electrode 200J. The VF−VR is calculated by the active measurement electrode 200J, and the result is transmitted wirelessly as the limb lead signal.

In addition, the active measurement electrode 200J outputs the potentials VF and VR of the electrocardiographic signals from output terminals 230 and 232 to the Wilson terminal 180.

The electrocardiograph body 300A uses the electrocardiographic signals sent from the active measurement electrodes 200-1 to 200-24, 200H and 200J of the limb and the chest to generate the body surface mapping ECG as shown in the figure. Traditional methods are used to generate the ECG of body surface mapping. The potential distribution around the heart can be seen visually by the body surface mapping ECG. And the abnormality of the heart can be found by observing the potential distribution state displayed by the body surface mapping ECG.

In the above embodiment, 24 electrodes of the chest are used as an example to explain the generation process of the body surface mapping ECG, but the body surface mapping ECG is not limited to using 24 chest electrodes, instead, 6 electrodes, 64 electrodes, 128 electrodes and so on, that is, more or less electrodes than 24 can also be used in practice.

Sixth Embodiment (Clothes that Make Up Electrocardiograph System)

Figure 30:
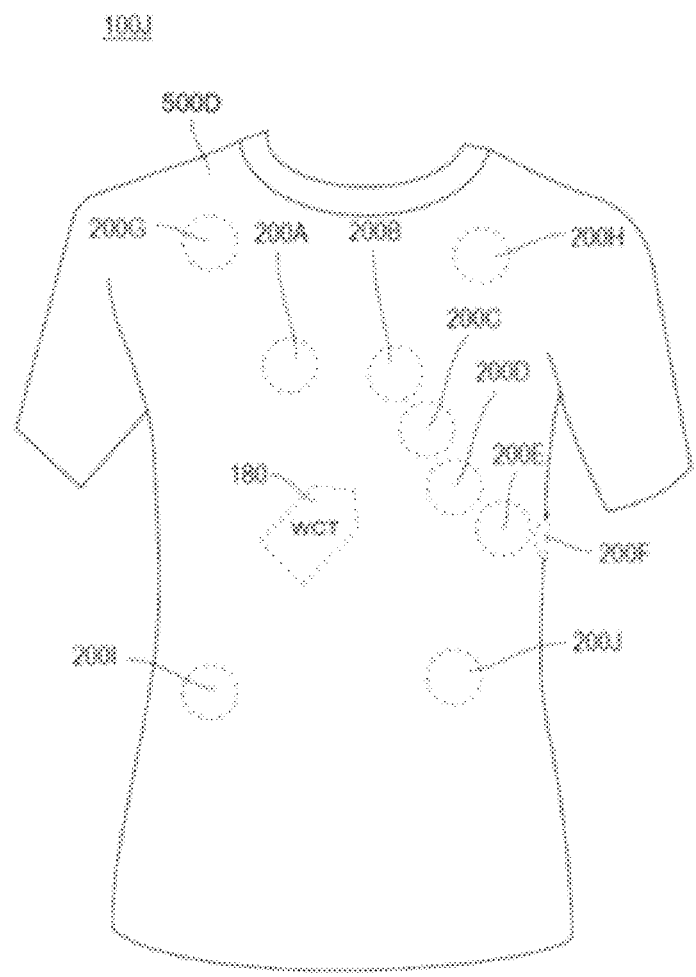
FIG. 30 is a structure diagram of clothes constituting an electrocardiograph system. (sixth embodiment).

FIG. 30 is a structure diagram of the clothes that configure the electrocardiograph system 100J of sixth embodiment. In sixth embodiment, the active measurement electrodes 200A-200F, 200H, 200J, passive measurement electrodes 200G, 200I and Wilson terminal 180 are embedded inside the T-shirt 500D.

In sixth embodiment, a T-shirt 500D is used as a garment. Unlike third embodiment, sixth embodiment does not open mounting holes on the T-shirt. In sixth embodiment, a T-shirt is illustrated as an example, but the embodiment need not to limited to using a T-shirt, instead, a Y-shirt, a polo shirt, etc. can also be used.

As shown in FIG. 30, inside the T-shirt 500D, the active measurement electrodes 200A-200F, 200H, 200J, and the passive measurement electrodes 200G, 200I and Wilson terminal 180 are configured to be embedded in the fabric of the T-shirt 500D.

The structure of the active measurement electrodes 200A-200F, 200H and 200J is similar to the structure of the active measurement electrodes illustrated in second embodiment shown in FIG. 17A. In addition, the structure of the passive measurement electrode 200G and 200I is similar to that of the passive measurement electrode illustrated in the second embodiment shown in FIG. 17B.

In sixth embodiment, the structure of the patch electrode which constitutes the active measurement electrode 200A-200F, 200H, 200J and the passive measurement electrode 200G, 200I is different from that of the first embodiment to the fifth embodiment.

(Configuration of Patch Electrode)

Figure 31A:
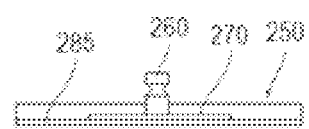
FIG. 31A is a side view of the patch electrodes constituting the active and passive measurement electrodes. (sixth embodiment).
Figure 31B:
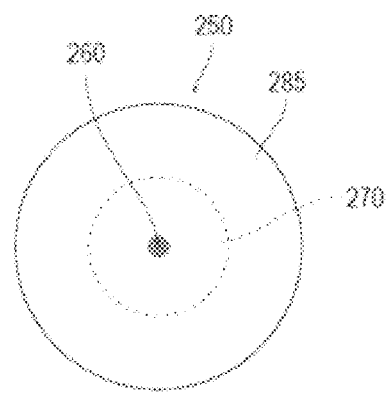
FIG. 31B is a bottom view of the patch electrodes constituting the active and passive measurement electrodes. (sixth embodiment).

FIG. 31A is a side view of the patch electrodes constituting the active and passive measurement electrodes. FIG. 31B is a bottom view of the patch electrodes constituting the active and passive measurement electrodes.

As shown in the FIGS. 31A and 31B, the patch electrode 250 includes a convex connector 260 which is electrically connected with the concave input terminals 220 of the control-communication devices 210 and 210b, and an electrode plate 270 placed at one end of the connector 260, as shown in FIGS. 17A and 17B. In the patch electrode of sixth embodiment, the conductive fiber cloth electrode 285 is pasted on the surface of the electrode plate 270. Conductive fiber cloth electrode 285 is formed by coating conductive polymer on the fiber, and has flexibility, elasticity, ventilation and excellent body affinity.

The patch electrode 250 is connected to the control communication-devices 210 and 210b shown in FIGS. 17A and 17B, and embedded inside the 500D of the T-shirt, used as the active measurement electrodes 200A-200F, 200H, 200J and the passive measurement electrodes 200G, 200I. The positions of active measurement electrodes 200A-200F, 200H, 200J and passive measurement electrodes 200G and 200I are the same as the positions of the electrodes for taking the 12-lead ECG.

Figure 32:
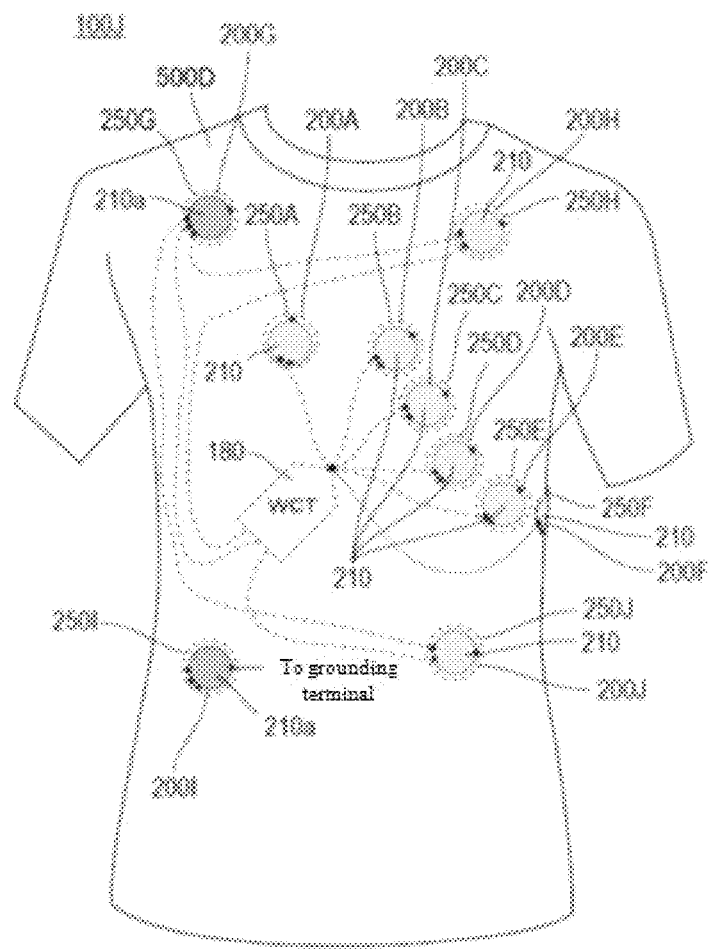
FIG. 32 is a diagram showing a scene where the measurement electrodes are placed on the chest and limbs inside the clothes. (sixth embodiment).

FIG. 32 is a diagram showing a state in which the measurement electrodes of chest and limbs are arranged inside clothes. As shown in FIG. 32, in the electrocardiograph system 100J of sixth embodiment, the active measurement electrodes 200A-200F, 200H, 200J and the passive measurement electrodes 200G, 200I and Wilson terminal 180 are pre-embedded into the inner side of the T-shirt 500D. In addition, the active measurement electrodes 200A-200F, 200H, 200J, passive measurement electrodes 200G, 200I and Wilson terminal 180 use conductive fiber lines sewn in the fiber of T-shirt 500D (dotted lines in the figure) to connect with each other. The conductive fiber line is formed by coating conductive polymer on the fiber material and immobilizing it.

The active measurement electrode 200A is configured by integrating the patch electrode 250A and the control-communication device 210, and is embedded in the illustrated position of the T-shirt 500D. The active measurement electrode 200B is configured by integrating the patch electrode 250B and the control-communication device 210, and is embedded in the illustrated position of the T-shirt 500D. The same applies to the active measurement electrodes 200C, 200D, 200E, 200F, 200H, and 200J. Also, the passive measurement electrode 200G is configured by integrating the patch electrode 250G and the control-communication device 210a, and is embedded in the illustrated position of the T-shirt 500D. The same applies to the passive measurement electrode 200I.

The positions to mount the active measurement electrodes 200A-200F, 200H, 200J and the passive measurement electrodes 200G, 200I on the T-shirt 500D are customized for the subject 150 in order to obtain the best electrocardiographic signal of the subject 150. The optimal positions of the active measurement electrodes 200A-200F, 200H, 200J and the passive measurement electrodes 200G, 200I vary depending on the subject 150.

As shown in FIG. 32, the T-shirt 500D is pre-configured with active measurement electrodes 200A-200F, 200H, 200J, passive measurement electrodes 200G, 200I and Wilson terminal 180, which are connected to each other with conductive fiber wires, thus, as long as the subject 150 wears the T-shirt 500D, the electrocardiograph system 100E of third embodiment shown in FIG. 23 can be simply realized.

In sixth embodiment, attaching and placing of active measurement electrodes 200A-200F, 200H, 200J, passive measurement electrodes 200G, 200I of the chest and the limb and Wilson terminal 180 are simplified by using T-shirt 500D. The actions of the electrocardiograph system are the same as those of the electrocardiograph system 100B (refer to FIG. 16) of second embodiment.

According to the electrocardiograph system 100J of sixth embodiment, the only thing the subject 150 needs to do is to wear T-shirt 500D for preparation of ECG measurement. Generally, medical education and training are required to correctly place electrodes when acquiring 12-lead ECG, but using T-shirt 500D the medical training is no longer necessary. Therefore, with the present embodiment, 12-lead ECG can be measured at home without having to go to the hospital. Further, since it is not necessary to attach the patch electrode using the conductive gel, it becomes possible to monitor the electrocardiogram on a daily basis without imposing a burden on the subject 150.

[Modification of Sixth Embodiment]

Figure 33:
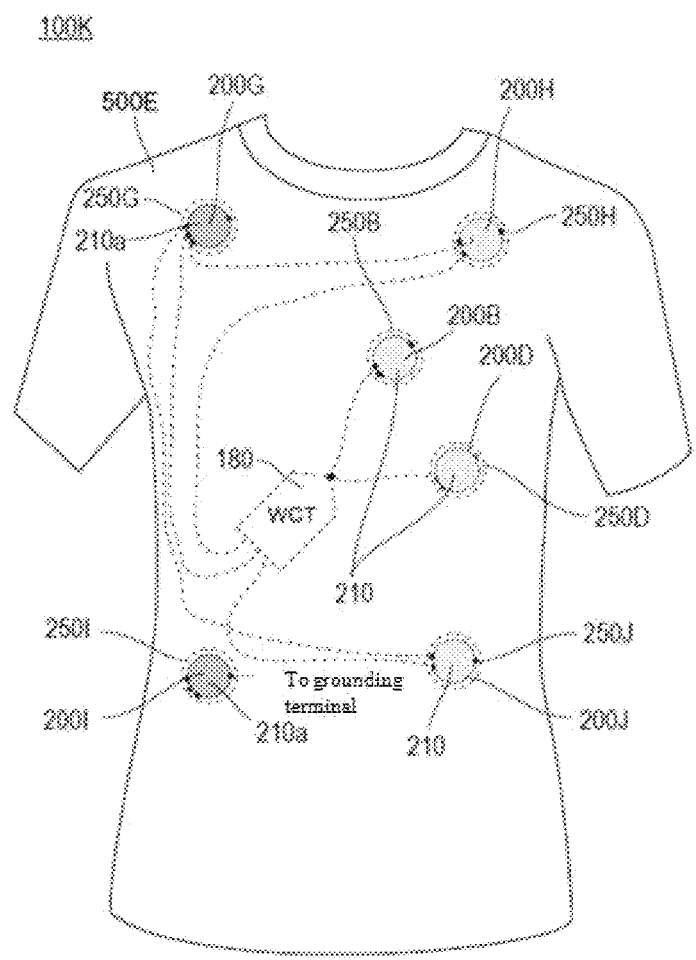
FIG. 33 is a diagram showing a modification of the electrocardiograph system of sixth embodiment.

FIG. 33 is a diagram showing a modification of the electrocardiograph system in sixth embodiment. In this modification, the T-shirt 500E is used as a garment. T-shirt 500E is equipped with active measurement electrodes 200B, 200D, 200H, 200J and passive measurement electrodes 200G and 200I.

In the modification of the electrocardiograph system in sixth embodiment, as long as subject 150 wears T-shirt 500E, the electrocardiograph system 100K same as the electrocardiograph system 100C of the modification of second embodiment shown in FIG. 18 can be realized.

In the modification of sixth embodiment, the use of T-shirt 500E simplifies the process to place the active measurement electrodes 200B, 200D, 200H, 200J, passive measurement electrodes 200G, 200I of the chest and the limb and Wilson terminal 180. The actions of the electrocardiograph systems, etc. is the same as the electrocardiograph system 100C (refer to FIG. 18) involved in the modification of second embodiment.

In this way, according to the electrocardiograph system 100K in the modification of sixth embodiment, the 4-lead ECG can be easily measured at home without going to the hospital. Although the V2 and V4 are used in the above example, of course, it is possible to use other chest leads such as V1 and V3.

Seventh Embodiment (Configuration of Electrocardiograph System)

Figure 34:
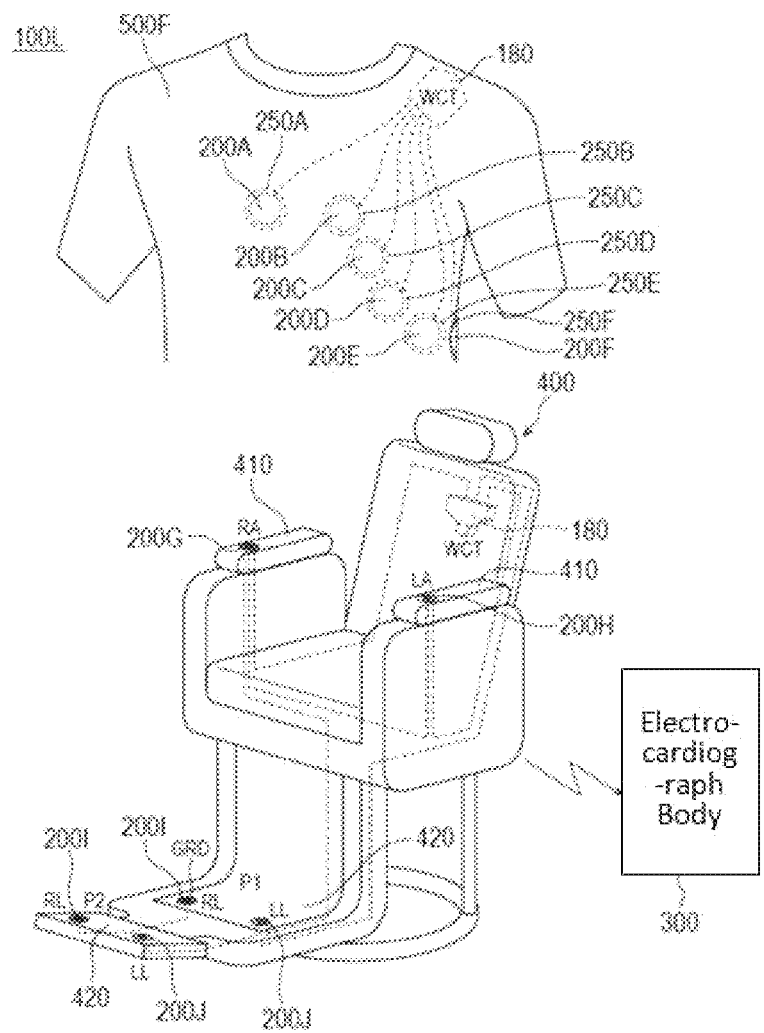
FIG. 34 is a structure diagram of an electrocardiograph system. (seventh embodiment).

FIG. 34 is a structure diagram of the electrocardiograph system 100L of seventh embodiment. In seventh embodiment, the active measurement electrodes 200A-200F and Wilson terminal 180 are embedded in T-shirt 500F, and the passive measurement electrodes 200G, 200I and active measurement electrodes 200H and 200J are configured on the chair 400. The electrocardiograph system 100L of seventh embodiment is a wearable electrocardiograph system. Electrocardiographic signals from active measurement electrodes 200A-200F, 200H, 200J and passive measurement electrodes 200G and 200I are transmitted to electrocardiograph body 300 through wireless transmission. The electrocardiograph body 300 generates the ECG of the subject 150 using the received electrocardiographic signal.

In the electrocardiograph system 100L of seventh embodiment, the subject 150 wears a T-shirt 500F and connects the T-shirt 500F to the Wilson terminal 180 of the chair 400. Then, sitting on the chair 400, the palms and the soles of the feet are brought into contact with the passive measurement electrodes 200G and 200I and the active measurement electrodes 200H and 200J. Thus, the electrocardiograph system 100G of fourth embodiment shown in FIG. 25 can be realized. The operation of the electrocardiograph system is the same as that of the electrocardiograph system 100A (see FIG. 15) according to the modification of First embodiment.

According to the electrocardiograph system 100L of Seventh embodiment, the measurement of the 12-lead ECG can be performed at home even without going to the hospital. In addition, since the 12-lead ECG can be measured by sitting on the chair 400, the subject 150 can take the electrocardiogram in a more relaxed state.

[Modification of Seventh Embodiment]

(Configuration of Electrocardiograph System)

Figure 35:
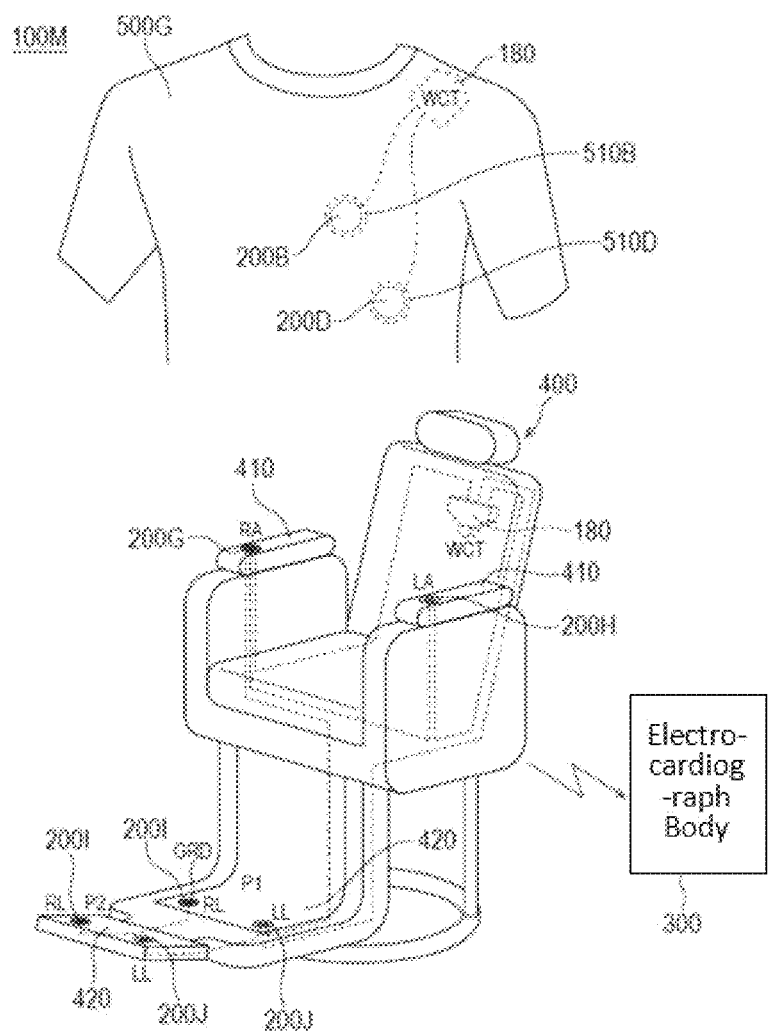
FIG. 35 is a diagram showing a modification of the electrocardiograph system of seventh embodiment.

FIG. 35 is a diagram showing a modification of the electrocardiograph system 100L of seventh embodiment. The 4-lead ECG is used in the modification of seventh embodiment. The active measurement electrodes 200B and 200D of electrocardiograph system 100M are embedded in T-shirt 500G. The electrocardiograph system 100M in the modification of seventh embodiment is also a wearable electrocardiograph system. The passive measurement electrodes 200G, 200I and active measurement electrodes 200H and 200J are arranged on the chair 400. The electrocardiographic signals from the active measurement electrodes 200B, 200D, 200H and 200J are transmitted to the electrocardiograph body 300 through wireless communications. The electrocardiograph body 300 generates the ECG of the subject 150 using the received electrocardiographic signals.

Even in this embodiment, similar to the electrocardiograph system 100G of fourth embodiment, the subject 150 wears a T-shirt 500G, and connects the T-shirt 500G to the Wilson terminal 180 of the chair 400. Then, subject 150 sits on the chair 400 to make the palms and the foot soles contacting the passive measurement electrodes 200G, 200I and the active measurement electrodes 200H, 200J.

Just in this way, the electrocardiograph system 100H, which takes the 4-lead ECG, involved in the modification of fourth embodiment shown in FIG. 26 can be realized. In this embodiment, the action of the electrocardiograph system is the same as that of the electrocardiograph system 100H (refer to FIG. 26) in the modification of fourth embodiment.

As illustrated, with the electrocardiograph system 100M involved in the modification example of seventh embodiment, ECG measurement for subject 150 does not have to be done at hospital, instead, can be easily done at home. In addition, lead V2 and V4 are used in the above embodiment, and other chest leads such as V1 and V3 can also be used.

Eighth Embodiment

Figure 36:
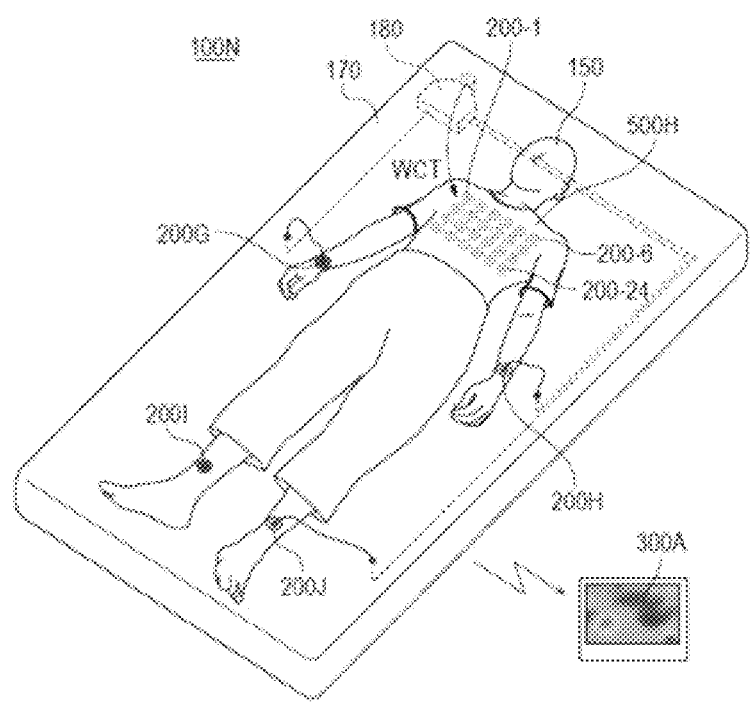
FIG. 36 is a structure diagram of an electrocardiograph system. (eighth embodiment).

FIG. 36 is a structure diagram of the electrocardiograph system 100N of eighth embodiment. As that of fifth embodiment shown in FIG. 28, the electrocardiograph system 100N of eighth embodiment is a system to take body surface mapping ECG.

In eighth embodiment, the T-shirt 500H worn by the subject 150 is provided with the active measurement electrodes 200-1 to 200-24 for acquiring the electrocardiographic signals of the subject 150.

As shown in FIG. 36, in the electrocardiograph system 100N according to eighth embodiment, first, the subject 150 wears the T-shirt 500H and lays on the bed 170. Next, a measurer attaches the passive measurement electrodes 200G and 200I and the active measurement electrodes 200H and 200J that acquire the electrocardiographic signals of the four limbs of the subject 150 to the four places of arms and legs. Next, a Wilson terminal 180 forming an indifferent electrode is provided by connecting to the passive measurement electrode 200G and the active measurement electrodes 200H and 200J attached to the right arm, left arm, and left leg of the subject 150. The passive measurement electrode 200G and the active measurement electrodes 200H and 200J are connected to the input part of the Wilson terminal 180, and the active measurement electrodes 200-1 to 200-24 are connected to the output part of the Wilson terminal 180.

The active measurement electrodes 200H and 200J transmit, in wireless communication, the limb lead signals which are obtained from the potentials of the electrocardiographic signals of the limbs acquired from the passive measurement electrodes 200G and 200I and the active measurement electrodes 200H and 200J. The active measurement electrodes 200-1 to 200-24 transmit, in wireless communication, the chest lead signals, which are obtained from the potentials of the electrocardiographic signals acquired by the active measurement electrodes 200-1 to 200-24 and the potentials of the indifferent electrodes of the Wilson terminal 180. The electrocardiograph body 300A generates the body surface mapping ECG as shown in the figure according to the chest lead signals sent by the active measurement electrode 200-1 to 200-24 and the limb lead signals sent by the active measurement electrode 200H and 200J.

The traditional methods are used to generate the body surface mapping ECG. The body surface mapping ECG can be used to visually see the distribution of cardiac peripheral potential, so abnormalities in the heart can be easily found by observing the distribution of potentials displayed by body surface mapping ECG.

In addition, in the above embodiment, the case that the 24 chest electrodes are used for the generation of the body surface mapping ECG is used for explanation as an example, the generation of the body surface mapping ECG is not limited to the 24 electrodes, and more electrodes than 24, for example, the 36 chest electrodes can also be used in practice.

As mentioned above, according to the electrocardiograph system, electrocardiographic measurement electrode and electrocardiographic measurement method of the invention, the lead signals generated by the active measurement electrode are transmitted through wireless communication, Thus, the problem that cables (usually long, thick and heavy) must be utilized in connection between the measurement electrodes and the host in previous electrocardiograph systems so far can be solved. Because the handling of the measurement electrode becomes better, it is easier to acquire the ECG of the subject.

In addition, according to the electrocardiograph system, electrocardiographic measurement electrode and electrocardiographic measurement method of the present invention, the correct ECG can be taken even when the active measurement electrode 200A-200F fall off or are incompletely installed. Thus, the application of 12-lead ECG test becomes easier in home medical treatment.

Furthermore, the technical scope of the invention of the electrocardiograph system, the electrocardiographic measurement electrode, and the electrocardiographic measurement method according to the present invention is not limited to the range described in the above embodiments and its modifications. It goes without saying that many other modified examples without departing from the technical scope of the invention are included in the present invention.

DESCRIPTION OF SYMBOLS 100, 100A-100N Electrocardiograph System,
150 Subject,
170 Bed,
180 Wilson Terminal,
200A-200F, 200H, 200J Active Measurement Electrode,
200G, 200I Passive Measurement Electrode,
200-1~200-24 Active Measurement Electrode,
210, 210a, 210b Control-Communication Device,
220, 225 Input Terminal,
230, 232 Output Terminal,
235 Ground Terminal,
240 ECG Generator
241 Amplifier,
242 A/D Converter,
243 Memory,
244 CPU,
245 Wireless Transmitter,
246 Battery,
250, 250a-250j Patch Electrode,
260 Connector,
270 Electrode Plate,
280 Conductive Gel.
285 Conductive Fiber Cloth Electrode,
300, 300A Electrocardiograph body,
310 Receiver,
320 Average Weight Database,
330 Optimal Weight Database,
340 Fall-Off Lead Weight Database,
350 Subject Information Database,
360 Controller,
370 Display,
400 Chair,
410 Armrest,
420 Footrest,
500, 500A-500G T-shirt.

What is claimed is:

1. An electrocardiograph system comprising:
a plurality of measurement electrodes for acquiring electrocardiographic signals of a subject;
a Wilson terminal for forming an indifferent electrode by connecting to the measurement electrodes; and
an electrocardiograph body for generating electrocardiograms, wherein
said plurality of measurement electrodes has a plurality of active measurement electrodes communicating with the electrocardiograph body through wireless communication, and a plurality of passive measurement electrodes connected with the active measurement electrodes and the Wilson terminal, and
the electrocardiograph body generates the electrocardiograms based on lead signals transmitted by the active measurement electrodes,
wherein, the electrocardiograph body comprises:
a receiver for receiving the lead signals transmitted by the active measurement electrodes;
an average weight database having stored thereon an average weight obtained from a population in order to generate the ECG of the subject in consideration of a fall-off of the active measurement electrodes;
an optimal weight database having stored thereon an optimal weight obtained from the subject in order to generate the ECG of the subject in consideration of the fall-off of the active measurement electrodes; and
a controller for identifying the fall-off of the active measurement electrodes from the subject according to the lead signals received from a receiver, interpolating the lead signals received by the receiver using the optimal weight, and generating the ECG inherent to the subject if the optimal weight database has the optimal weight acquired from the subject, and otherwise if the optimal weight of the subject does not exist in the optimal weight database, interpolating the lead signals received by the receiver using the average weight in the average weight database, and generating the ECG of the subject.

2. The electrocardiograph system according to claim 1, wherein
the active measurement electrodes are a device integrated with a patch electrode for acquiring the electrocardiographic signals of the subject and a control-communication device for processing the electrocardiographic signals, and
the control-communication device comprises:
an input terminal for inputting electrocardiographic signals from the patch electrode and the Wilson terminal;
an ECG generator for generating the lead signals with using input electrocardiographic signals; and
a wireless transmitter for transmitting the generated lead signals externally.

3. The electrocardiograph system according to claim 2, wherein
the control-communication device further includes an input terminal for inputting the electrocardiographic signals from the passive measurement electrodes.

4. The electrocardiograph system according to claim 3, wherein the ECG generator comprises:
an amplifier for amplifying the input electrocardiographic signals;
an A/D converter for converting the amplified electrocardiographic signals to digital signals; and
a CPU for calculating the lead signals with using the digital signals converted from the electrocardiographic signals.

5. The electrocardiograph system according to claim 2, wherein
the ECG generator comprises:
an amplifier for amplifying the input electrocardiographic signals;
an A/D converter for converting the amplified electrocardiographic signals to digital signals; and
a CPU for calculating the lead signals with using the digital signals converted from the electrocardiographic signals.

6. The electrocardiograph system according to claim 2, wherein
the wireless communication used by the wireless transmitter for transmitting lead signals outward is performed by any one of infrared ray, wireless LAN and Bluetooth®.

7. The electrocardiograph system according to claim 1, wherein
the passive measurement electrodes are a device integrated with a patch electrode for acquiring the electrocardiographic signals of the subject and a control-communication device for outputting the electrocardiographic signals, and
the control-communication device comprises:
an input terminal for inputting the electrocardiographic signals from the patch electrode; and
an output terminal for outputting the electrocardiographic signals which is input from the input terminal to the active measurement electrodes or Wilson terminal.

8. The electrocardiograph system according to claim 1, wherein
the average weight database stores the average weight corresponding to all possible cases where one or more active measurement electrodes fall off, the optimal weight database stores the optimal weight corresponding to all possible cases where one or more active measurement electrodes fall off, and
the controller identifies the case in which electrodes fall off based on the lead signals received from the receiver, and takes the average weight or optimal weight from the average weight database or the optimal weight database according to the case.

9. The electrocardiograph system according to claim 1, wherein
the electrocardiograph body further includes a subject information database, which at least stores the information of name, gender and age of the subjects,
the average weight database stores the average weight according to gender and age, and
the controller takes the optimal weight of the subject from the optimal weight database or takes the average weight suitable for the gender and age of the subject from the average weight database with reference to the information of the subject.

10. The electrocardiograph system according to claim 1, wherein
the ECG generated by the controller is any of 12-lead ECG, 4-lead ECG, 3-lead ECG or body surface mapping ECG, and the electrocardiograph body further has a display for displaying the ECG.

11. The electrocardiograph system according to claim 1, wherein
a chair on which the subject sits during an electrocardiographic measurement is provided,
the measurement electrodes are arranged on an armrest and a footrest of the chair, and
the Wilson terminal is embedded in the interior of the chair, and forms the indifferent electrode by connecting to each of the measurement electrodes on the armrest and the footrest of the chair, respectively.

12. The electrocardiograph system according to claim 11, wherein
the chair is adjustable for its inclination,
the footrest is provided with a plurality of separate footrests, so that the feet of the subject can use different foot placement positions according to inclination angles,
the measurement electrodes are respectively arranged at each of the plurality of footrests, and
among the measurement electrodes arranged at each of the footrests, usable measurement electrodes can switch according to the inclination angle.

13. The electrocardiograph system according to claim 1, wherein:
a chair on which the subject sits during an electrocardiographic measurement and clothes which has a plurality of mounting holes indicating mounting positions of the measurement electrodes are provided,
a patch electrode of the measurement electrodes is attached inside the mounting holes of the clothes worn by the subject,
the Wilson terminal connected with the measurement electrodes is embedded in the clothes,
the measurement electrodes are positioned inside the mounting holes of the clothes and on the armrest and footrest of the chair,
the Wilson terminal connected with the measurement electrodes are embedded in the chair, and the input part of the Wilson terminal embedded in the clothes and the output part of the Wilson terminal embedded in the chair are electrically connected by wires.

14. The electrocardiograph system according to claim 13, wherein the chair is adjustable for its inclination, a plurality of separate footrests are provided, so that the feet of the subject can use different foot placement positions according to inclination angles, the measurement electrodes are respectively arranged at each of the plurality of footrests, and among the measurement electrodes arranged at each of footrests, usable measurement electrodes can switch according to the inclination angle.

15. The electrocardiograph system according to claim 1, wherein clothes are further provided with a plurality of mounting holes indicating mounting positions for the active measurement electrodes and the passive measurement electrodes, the active measurement electrodes and the passive measurement electrodes are arranged in the mounting holes of the clothes worn by the subject, and the Wilson terminal is embedded in the clothes.

16. The electrocardiograph system according to claim 1, wherein a chair on which the subject sits during an electrocardiographic measurement and clothes embedded with said plurality of measurement electrodes and Wilson terminal are further provided, the plurality of measurement electrodes and Wilson terminal embedded in the clothes are connected to each other through conductive fiber lines, the plurality of measurement electrodes are also arranged on the armrest and the footrest of the chair, the Wilson terminal connected with the measurement electrodes is embedded in the chair, and the input terminal of the Wilson terminal embedded in the clothing is connected with the output terminal of the Wilson terminal embedded in the chair through a wire.

17. The electrocardiograph system according to claim 16, wherein the chair is adjustable for its inclination, the footrest is provided with a plurality of separate footrests, so that the feet of the subject can use different foot placement positions according to inclination angles, the measurement electrodes are respectively arranged at each of the plurality of footrests, and among the measurement electrodes arranged at each of the footrests, usable measurement electrodes can switch according to the inclination angle.

* * * * *